US012765942B2

(12) United States Patent
Carlson et al.

(10) Patent No.: US 12,765,942 B2
(45) Date of Patent: Oct. 20, 2026

(54) ENERGY COUPLING MITIGATION DEVICE AND RELATED SYSTEMS AND METHODS

(71) Applicant: Virtual Incision Corporation, Lincoln, NE (US)

(72) Inventors: Jay Carlson, Lincoln, NE (US); Shane Farritor, Lincoln, NE (US)

(73) Assignee: VIRTUAL INCISION CORPORATION, Lincoln, NE (US)

( * ) Notice: Subject to any disclaimer, the term of this patent is extended or adjusted under 35 U.S.C. 154(b) by 585 days.

(21) Appl. No.: 18/299,129

(22) Filed: Apr. 12, 2023

(65) Prior Publication Data

US 2023/0320778 A1 Oct. 12, 2023

Related U.S. Application Data

(60) Provisional application No. 63/329,914, filed on Apr. 12, 2022.

(51) Int. Cl.

| | |
|---|---|
| ***A61B 18/14*** | (2006.01) |
| ***A61B 34/30*** | (2016.01) |
| *A61B 18/00* | (2006.01) |

(52) U.S. Cl.

CPC .......... *A61B 18/1482* (2013.01); *A61B 34/30* (2016.02); *A61B 2018/00708* (2013.01); *A61B 2018/00827* (2013.01)

(58) Field of Classification Search

CPC ...... A61B 18/1482; A61B 2018/00178; A61B 2018/00708; A61B 2018/00827; A61B 34/30

See application file for complete search history.

(56) References Cited

U.S. PATENT DOCUMENTS

| | | | |
|---|---|---|---|
| 3,870,264 | A | 3/1975 | Robinson |
| 3,989,952 | A | 11/1976 | Hohmann |
| 4,246,661 | A | 1/1981 | Pinson |
| 4,258,716 | A | 3/1981 | Sutherland |
| 4,278,077 | A | 7/1981 | Mizumoto |
| 4,538,594 | A | 9/1985 | Boebel et al. |
| 4,568,311 | A | 2/1986 | Miyake |

(Continued)

FOREIGN PATENT DOCUMENTS

| | | | |
|---|---|---|---|
| CA | 2690808 | C | 9/2016 |
| CN | 102821918 | A | 12/2012 |

(Continued)

OTHER PUBLICATIONS

Kang et al., "Robotic Assistants Aid Surgeons During Minimally Invasive Procedures," IEEE Engineering in Medicine and Biology, Jan.-Feb. 2001; pp. 94-104.

(Continued)

*Primary Examiner* — Tigist S Demie

(74) *Attorney, Agent, or Firm* — Fredrikson & Byron, P.A.

(57) ABSTRACT

Surgical systems having an end effector, a conductor, and a disconnection mechanism associated with the at least one conductor, wherein the mechanism is configured to electrically disconnect the end effector from an energy source when not in use so as to reduce energy leakage out of the instrument. Other embodiments include various robotic surgical devices having a disconnection mechanism. Further implementations include methods of mitigating energy coupling during use of a robotic surgical device.

20 Claims, 7 Drawing Sheets

(56) References Cited

U.S. PATENT DOCUMENTS

| | | | |
|---|---|---|---|
| 4,579,476 | A | 4/1986 | Post |
| 4,623,183 | A | 11/1986 | Aomori |
| 4,736,645 | A | 4/1988 | Zimmer |
| 4,771,652 | A | 9/1988 | Zimmer |
| 4,852,391 | A | 8/1989 | Ruch et al. |
| 4,896,015 | A | 1/1990 | Taboada et al. |
| 4,897,014 | A | 1/1990 | Tietze |
| 4,922,755 | A | 5/1990 | Oshiro et al. |
| 4,922,782 | A | 5/1990 | Kawai |
| 4,990,050 | A | 2/1991 | Tsuge et al. |
| 5,019,968 | A | 5/1991 | Wang et al. |
| 5,108,140 | A | 4/1992 | Bartholet |
| 5,172,639 | A | 12/1992 | Wiesman et al. |
| 5,176,649 | A | 1/1993 | Wakabayashi |
| 5,178,032 | A | 1/1993 | Zona et al. |
| 5,187,032 | A | 2/1993 | Sasaki et al. |
| 5,187,796 | A | 2/1993 | Wang et al. |
| 5,195,388 | A | 3/1993 | Zona et al. |
| 5,201,325 | A | 4/1993 | Mcewen et al. |
| 5,217,003 | A | 6/1993 | Wilk |
| 5,263,382 | A | 11/1993 | Brooks et al. |
| 5,271,384 | A | 12/1993 | Mcewen et al. |
| 5,284,096 | A | 2/1994 | Pelrine et al. |
| 5,297,443 | A | 3/1994 | Wentz |
| 5,297,536 | A | 3/1994 | Wilk |
| 5,304,899 | A | 4/1994 | Sasaki et al. |
| 5,307,447 | A | 4/1994 | Asano et al. |
| 5,353,807 | A | 10/1994 | Demarco |
| 5,363,935 | A | 11/1994 | Schempf et al. |
| 5,382,885 | A | 1/1995 | Salcudean et al. |
| 5,388,528 | A | 2/1995 | Pelrine et al. |
| 5,436,542 | A | 7/1995 | Petelin et al. |
| 5,441,494 | A | 8/1995 | Ortiz |
| 5,458,131 | A | 10/1995 | Wilk |
| 5,458,583 | A | 10/1995 | Mcneely et al. |
| 5,458,598 | A | 10/1995 | Feinberg et al. |
| 5,462,546 | A | 10/1995 | Rydell |
| 5,471,515 | A | 11/1995 | Fossum et al. |
| 5,515,478 | A | 5/1996 | Wang |
| 5,522,669 | A | 6/1996 | Recker |
| 5,524,180 | A | 6/1996 | Wang et al. |
| 5,553,198 | A | 9/1996 | Wang et al. |
| 5,562,448 | A | 10/1996 | Mushabac |
| 5,588,442 | A | 12/1996 | Scovil et al. |
| 5,620,417 | A | 4/1997 | Jang et al. |
| 5,623,582 | A | 4/1997 | Rosenberg |
| 5,624,380 | A | 4/1997 | Kaneko et al. |
| 5,624,398 | A | 4/1997 | Smith et al. |
| 5,632,761 | A | 5/1997 | Smith et al. |
| 5,645,520 | A | 7/1997 | Nakamura et al. |
| 5,657,429 | A | 8/1997 | Wang et al. |
| 5,657,584 | A | 8/1997 | Hamlin |
| 5,672,168 | A | 9/1997 | De La Torre et al. |
| 5,674,030 | A | 10/1997 | Sigel |
| 5,728,599 | A | 3/1998 | Rostoker et al. |
| 5,736,821 | A | 4/1998 | Suyama |
| 5,754,741 | A | 5/1998 | Wang et al. |
| 5,762,458 | A | 6/1998 | Wang et al. |
| 5,769,640 | A | 6/1998 | Jacobus et al. |
| 5,791,231 | A | 8/1998 | Cohn et al. |
| 5,792,135 | A | 8/1998 | Madhani et al. |
| 5,797,538 | A | 8/1998 | Heaton et al. |
| 5,797,900 | A | 8/1998 | Madhani et al. |
| 5,807,377 | A | 9/1998 | Madhani et al. |
| 5,808,665 | A | 9/1998 | Green |
| 5,815,640 | A | 9/1998 | Wang et al. |
| 5,825,982 | A | 10/1998 | Wright et al. |
| 5,841,950 | A | 11/1998 | Wang et al. |
| 5,845,646 | A | 12/1998 | Lemelson |
| 5,855,583 | A | 1/1999 | Wang et al. |
| 5,876,325 | A | 3/1999 | Mizuno et al. |
| 5,878,193 | A | 3/1999 | Wang et al. |
| 5,878,783 | A | 3/1999 | Smart |
| 5,895,417 | A | 4/1999 | Pomeranz et al. |
| 5,906,591 | A | 5/1999 | Dario et al. |
| 5,907,664 | A | 5/1999 | Wang et al. |
| 5,910,129 | A | 6/1999 | Koblish et al. |
| 5,911,036 | A | 6/1999 | Wright et al. |
| 5,913,874 | A | 6/1999 | Berns et al. |
| 5,971,976 | A | 10/1999 | Wang et al. |
| 5,993,467 | A | 11/1999 | Yoon |
| 6,001,108 | A | 12/1999 | Wang et al. |
| 6,007,550 | A | 12/1999 | Wang et al. |
| 6,030,365 | A | 2/2000 | Laufer |
| 6,031,371 | A | 2/2000 | Smart |
| 6,058,323 | A | 5/2000 | Lemelson |
| 6,063,095 | A | 5/2000 | Wang et al. |
| 6,066,090 | A | 5/2000 | Yoon |
| 6,086,529 | A | 7/2000 | Arndt |
| 6,102,850 | A | 8/2000 | Wang et al. |
| 6,107,795 | A | 8/2000 | Smart |
| 6,113,596 | A | 9/2000 | Hooven et al. |
| 6,132,368 | A | 10/2000 | Cooper |
| 6,132,441 | A | 10/2000 | Grace |
| 6,139,563 | A | 10/2000 | Cosgrove et al. |
| 6,156,006 | A | 12/2000 | Brosens et al. |
| 6,159,146 | A | 12/2000 | El Gazayerli |
| 6,162,171 | A | 12/2000 | Ng et al. |
| D438,617 | S | 3/2001 | Cooper et al. |
| 6,206,903 | B1 | 3/2001 | Ramans |
| D441,076 | S | 4/2001 | Cooper et al. |
| 6,223,100 | B1 | 4/2001 | Green |
| D441,862 | S | 5/2001 | Cooper et al. |
| 6,238,415 | B1 | 5/2001 | Sepetka et al. |
| 6,240,312 | B1 | 5/2001 | Alfano et al. |
| 6,241,730 | B1 | 6/2001 | Alby |
| 6,244,809 | B1 | 6/2001 | Wang et al. |
| 6,246,200 | B1 | 6/2001 | Blumenkranz et al. |
| D444,555 | S | 7/2001 | Cooper et al. |
| 6,286,514 | B1 | 9/2001 | Lemelson |
| 6,292,678 | B1 | 9/2001 | Hall et al. |
| 6,293,282 | B1 | 9/2001 | Lemelson |
| 6,296,635 | B1 | 10/2001 | Smith et al. |
| 6,309,397 | B1 | 10/2001 | Julian et al. |
| 6,309,403 | B1 | 10/2001 | Minor et al. |
| 6,312,435 | B1 | 11/2001 | Wallace et al. |
| 6,321,106 | B1 | 11/2001 | Lemelson |
| 6,327,492 | B1 | 12/2001 | Lemelson |
| 6,331,181 | B1 | 12/2001 | Tierney et al. |
| 6,346,072 | B1 | 2/2002 | Cooper |
| 6,352,503 | B1 | 3/2002 | Matsui et al. |
| 6,364,888 | B1 | 4/2002 | Niemeyer et al. |
| 6,371,952 | B1 | 4/2002 | Madhani et al. |
| 6,394,998 | B1 | 5/2002 | Wallace et al. |
| 6,398,726 | B1 | 6/2002 | Ramans et al. |
| 6,400,980 | B1 | 6/2002 | Lemelson |
| 6,408,224 | B1 | 6/2002 | Okamoto et al. |
| 6,424,885 | B1 | 7/2002 | Niemeyer et al. |
| 6,432,112 | B2 | 8/2002 | Brock et al. |
| 6,436,107 | B1 | 8/2002 | Wang et al. |
| 6,441,577 | B2 | 8/2002 | Blumenkranz et al. |
| 6,450,104 | B1 | 9/2002 | Grant et al. |
| 6,451,027 | B1 | 9/2002 | Cooper et al. |
| 6,454,758 | B1 | 9/2002 | Thompson et al. |
| 6,459,926 | B1 | 10/2002 | Nowlin et al. |
| 6,463,361 | B1 | 10/2002 | Wang et al. |
| 6,468,203 | B2 | 10/2002 | Belson |
| 6,468,265 | B1 | 10/2002 | Evans et al. |
| 6,470,236 | B2 | 10/2002 | Ohtsuki |
| 6,478,681 | B1 | 11/2002 | Overaker et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,496,099 | B2 | 12/2002 | Wang et al. |
| 6,497,651 | B1 | 12/2002 | Kan et al. |
| 6,508,413 | B2 | 1/2003 | Bauer et al. |
| 6,512,345 | B2 | 1/2003 | Borenstein et al. |
| 6,522,906 | B1 | 2/2003 | Salisbury et al. |
| 6,544,276 | B1 | 4/2003 | Azizi |
| 6,548,982 | B1 | 4/2003 | Papanikolopoulos et al. |
| 6,554,790 | B1 | 4/2003 | Moll |
| 6,565,554 | B1 | 5/2003 | Niemeyer |
| 6,574,355 | B2 | 6/2003 | Green |
| 6,587,750 | B2 | 7/2003 | Gerbi et al. |

(56) References Cited

U.S. PATENT DOCUMENTS 6,591,239 B1 7/2003 Mccall et al.
6,594,552 B1 7/2003 Nowlin et al.
6,610,007 B2 8/2003 Belson et al.
6,620,173 B2 9/2003 Gerbi et al.
6,642,836 B1 11/2003 Wang et al.
6,645,196 B1 11/2003 Nixon et al.
6,646,541 B1 11/2003 Wang et al.
6,648,814 B2 11/2003 Kim et al.
6,659,939 B2 12/2003 Moll et al.
6,661,571 B1 12/2003 Shioda et al.
6,671,581 B2 12/2003 Niemeyer et al.
6,676,684 B1 1/2004 Morley et al.
6,684,129 B2 1/2004 Salisbury et al.
6,685,648 B2 2/2004 Flaherty et al.
6,685,698 B2 2/2004 Morley et al.
6,687,571 B1 2/2004 Byrne et al.
6,692,485 B1 2/2004 Brock et al.
6,699,177 B1 3/2004 Wang et al.
6,699,235 B2 3/2004 Wallace et al.
6,702,734 B2 3/2004 Kim et al.
6,702,805 B1 3/2004 Stuart
6,714,839 B2 3/2004 Salisbury et al.
6,714,841 B1 3/2004 Wright et al.
6,719,684 B2 4/2004 Kim et al.
6,720,988 B1 4/2004 Gere et al.
6,726,699 B1 4/2004 Wright et al.
6,728,599 B2 4/2004 Wang et al.
6,730,021 B2 5/2004 Vassiliades et al.
6,731,988 B1 5/2004 Green
6,746,443 B1 6/2004 Morley et al.
6,764,441 B2 7/2004 Chiel et al.
6,764,445 B2 7/2004 Ramans et al.
6,766,204 B2 7/2004 Niemeyer et al.
6,770,081 B1 8/2004 Cooper et al.
6,774,597 B1 8/2004 Borenstein
6,776,165 B2 8/2004 Jin
6,780,184 B2 8/2004 Tanrisever
6,783,524 B2 8/2004 Anderson et al.
6,785,593 B2 8/2004 Wang et al.
6,788,018 B1 9/2004 Blumenkranz
6,792,663 B2 9/2004 Krzyzanowski
6,793,653 B2 9/2004 Sanchez et al.
6,799,065 B1 9/2004 Niemeyer
6,799,088 B2 9/2004 Wang et al.
6,801,325 B2 10/2004 Farr et al.
6,804,581 B2 10/2004 Wang et al.
6,810,281 B2 10/2004 Brock et al.
6,817,972 B2 11/2004 Snow
6,817,974 B2 11/2004 Cooper et al.
6,817,975 B1 11/2004 Farr et al.
6,820,653 B1 11/2004 Schempf et al.
6,824,508 B2 11/2004 Kim et al.
6,824,510 B2 11/2004 Kim et al.
6,832,988 B2 12/2004 Sproul
6,832,996 B2 12/2004 Woloszko et al.
6,836,703 B2 12/2004 Wang et al.
6,837,846 B2 1/2005 Jaffe et al.
6,837,883 B2 1/2005 Moll et al.
6,839,612 B2 1/2005 Sanchez et al.
6,840,938 B1 1/2005 Morley et al.
6,852,107 B2 2/2005 Wang et al.
6,858,003 B2 2/2005 Evans et al.
6,860,346 B2 3/2005 Burt et al.
6,860,877 B1 3/2005 Sanchez et al.
6,866,671 B2 3/2005 Tierney et al.
6,870,343 B2 3/2005 Borenstein et al.
6,871,117 B2 3/2005 Wang et al.
6,871,563 B2 3/2005 Choset et al.
6,879,880 B2 4/2005 Nowlin et al.
6,892,112 B2 5/2005 Wang et al.
6,899,705 B2 5/2005 Niemeyer
6,902,560 B1 6/2005 Morley et al.
6,905,460 B2 6/2005 Wang et al.
6,905,491 B1 6/2005 Wang et al.
6,911,916 B1 6/2005 Wang et al.
6,917,176 B2 7/2005 Schempf et al.
6,933,695 B2 8/2005 Blumenkranz
6,936,001 B1 8/2005 Snow
6,936,003 B2 8/2005 Iddan
6,936,042 B2 8/2005 Wallace et al.
6,943,663 B2 9/2005 Wang et al.
6,949,096 B2 9/2005 Davison et al.
6,951,535 B2 10/2005 Ghodoussi et al.
6,965,812 B2 11/2005 Wang et al.
6,974,411 B2 12/2005 Belson
6,974,449 B2 12/2005 Niemeyer
6,979,423 B2 12/2005 Moll
6,984,203 B2 1/2006 Tartaglia et al.
6,984,205 B2 1/2006 Gazdzinski
6,991,627 B2 1/2006 Madhani et al.
6,993,413 B2 1/2006 Sunaoshi
6,994,703 B2 2/2006 Wang et al.
6,994,708 B2 2/2006 Manzo
6,997,908 B2 2/2006 Carrillo, Jr. et al.
7,025,064 B2 4/2006 Wang et al.
7,027,892 B2 4/2006 Wang et al.
7,033,344 B2 4/2006 Imran
7,039,453 B2 5/2006 Mullick et al.
7,042,184 B2 5/2006 Oleynikov et al.
7,048,745 B2 5/2006 Tierney et al.
7,053,752 B2 5/2006 Wang et al.
7,063,682 B1 6/2006 Whayne et al.
7,066,879 B2 6/2006 Fowler et al.
7,066,926 B2 6/2006 Wallace et al.
7,074,179 B2 7/2006 Wang et al.
7,077,446 B2 7/2006 Kameda et al.
7,083,571 B2 8/2006 Wang et al.
7,083,615 B2 8/2006 Peterson et al.
7,087,049 B2 8/2006 Nowlin et al.
7,090,683 B2 8/2006 Brock et al.
7,097,640 B2 8/2006 Wang et al.
7,105,000 B2 9/2006 Mcbrayer
7,107,090 B2 9/2006 Salisbury, Jr. et al.
7,109,678 B2 9/2006 Kraus et al.
7,118,582 B1 10/2006 Wang et al.
7,121,781 B2 10/2006 Sanchez
7,125,403 B2 10/2006 Julian et al.
7,126,303 B2 10/2006 Farritor et al.
7,147,650 B2 12/2006 Lee
7,155,315 B2 12/2006 Niemeyer et al.
7,169,141 B2 1/2007 Brock et al.
7,182,025 B2 2/2007 Ghorbel et al.
7,182,089 B2 2/2007 Ries
7,199,545 B2 4/2007 Oleynikov et al.
7,206,626 B2 4/2007 Quaid
7,206,627 B2 4/2007 Abovitz et al.
7,210,364 B2 5/2007 Ghorbel et al.
7,214,230 B2 5/2007 Brock et al.
7,217,240 B2 5/2007 Snow
7,239,940 B2 7/2007 Wang et al.
7,250,028 B2 7/2007 Julian et al.
7,259,652 B2 8/2007 Wang et al.
7,273,488 B2 9/2007 Nakamura et al.
7,311,107 B2 12/2007 Harel et al.
7,339,341 B2 3/2008 Oleynikov et al.
7,372,229 B2 5/2008 Farritor et al.
7,447,537 B1 11/2008 Funda et al.
7,492,116 B2 2/2009 Oleynikov et al.
7,566,300 B2 7/2009 Devierre et al.
7,574,250 B2 8/2009 Niemeyer
7,637,905 B2 12/2009 Saadat et al.
7,645,230 B2 1/2010 Mikkaichi et al.
7,655,004 B2 2/2010 Long
7,670,329 B2 3/2010 Flaherty et al.
7,731,727 B2 6/2010 Sauer
7,762,825 B2 7/2010 Burbank et al.
7,772,796 B2 8/2010 Farritor et al.
7,785,251 B2 8/2010 Wilk
7,785,333 B2 8/2010 Miyamoto et al.
7,789,825 B2 9/2010 Nobis et al.
7,794,494 B2 9/2010 Sahatjian et al.
7,865,266 B2 1/2011 Moll et al.
7,960,935 B2 6/2011 Farritor et al.
8,021,358 B2 9/2011 Doyle et al.

(56) References Cited

U.S. PATENT DOCUMENTS 8,179,073 B2 5/2012 Farritor et al.
8,231,610 B2 7/2012 Jo et al.
8,343,171 B2 1/2013 Farritor et al.
8,353,897 B2 1/2013 Doyle et al.
8,679,096 B2 3/2014 Farritor et al.
8,828,024 B2 9/2014 Farritor et al.
8,834,488 B2 9/2014 Farritor et al.
8,894,633 B2 11/2014 Farritor et al.
8,968,267 B2 3/2015 Nelson et al.
8,968,332 B2 3/2015 Farritor et al.
8,974,440 B2 3/2015 Farritor et al.
9,010,214 B2 4/2015 Markvicka et al.
9,060,781 B2 6/2015 Farritor et al.
9,089,353 B2 7/2015 Farritor et al.
9,179,981 B2 11/2015 Farritor et al.
9,427,282 B2 8/2016 Belson et al.
9,498,292 B2 11/2016 Mondry et al.
9,579,088 B2 2/2017 Farritor et al.
9,649,020 B2 5/2017 Finlay
9,743,987 B2 8/2017 Farritor et al.
9,757,187 B2 9/2017 Farritor et al.
9,770,305 B2 9/2017 Farritor et al.
9,883,911 B2 2/2018 Farritor et al.
9,888,966 B2 2/2018 Farritor et al.
9,956,073 B2 5/2018 Haddock et al.
10,111,711 B2 10/2018 Farritor et al.
10,219,870 B2 3/2019 Mondry et al.
10,307,199 B2 6/2019 Farritor et al.
10,335,024 B2 7/2019 Rentschler et al.
10,342,561 B2 7/2019 Farritor et al.
10,376,322 B2 8/2019 Frederick et al.
10,470,828 B2 11/2019 Markvicka et al.
10,582,973 B2 3/2020 Wilson et al.
10,667,883 B2 6/2020 Farritor et al.
10,675,110 B2 6/2020 Farritor et al.
10,702,347 B2 7/2020 Farritor et al.
10,722,319 B2 7/2020 Farritor et al.
10,751,136 B2 8/2020 Farritor et al.
10,806,538 B2 10/2020 Farritor et al.
10,966,700 B2 4/2021 Farritor et al.
11,013,564 B2 5/2021 Palmowski et al.
11,065,050 B2 7/2021 Farritor et al.
11,166,758 B2 11/2021 Mohr et al.
11,903,658 B2 2/2024 Farritor et al.
2001/0018591 A1 8/2001 Brock et al.
2001/0049497 A1 12/2001 Kalloo et al.
2002/0003173 A1 1/2002 Bauer et al.
2002/0013601 A1 1/2002 Nobles et al.
2002/0026186 A1 2/2002 Woloszko et al.
2002/0038077 A1 3/2002 De La Torre et al.
2002/0065507 A1 5/2002 Zadno-Azizi
2002/0091374 A1 7/2002 Cooper
2002/0103417 A1 8/2002 Gazdzinski
2002/0111535 A1 8/2002 Kim et al.
2002/0120254 A1 8/2002 Julian et al.
2002/0128552 A1 9/2002 Nowlin et al.
2002/0140392 A1 10/2002 Borenstein et al.
2002/0147487 A1 10/2002 Sundquist et al.
2002/0151906 A1 10/2002 Demarais et al.
2002/0156347 A1 10/2002 Kim et al.
2002/0171385 A1 11/2002 Kim et al.
2002/0173700 A1 11/2002 Kim et al.
2002/0190682 A1 12/2002 Schempf et al.
2003/0020810 A1 1/2003 Takizawa et al.
2003/0045888 A1 3/2003 Brock et al.
2003/0065250 A1 4/2003 Chiel et al.
2003/0089267 A1 5/2003 Ghorbel et al.
2003/0092964 A1 5/2003 Kim et al.
2003/0097129 A1 5/2003 Davison et al.
2003/0100817 A1 5/2003 Wang et al.
2003/0114731 A1 6/2003 Cadeddu et al.
2003/0135203 A1 7/2003 Wang et al.
2003/0139742 A1 7/2003 Wampler et al.
2003/0144656 A1 7/2003 Ocel et al.
2003/0159535 A1 8/2003 Grover et al.
2003/0167000 A1 9/2003 Mullick et al.
2003/0172871 A1 9/2003 Scherer
2003/0179308 A1 9/2003 Zamorano et al.
2003/0181788 A1 9/2003 Yokoi et al.
2003/0229268 A1 12/2003 Uchiyama et al.
2003/0229338 A1 12/2003 Irion et al.
2003/0230372 A1 12/2003 Schmidt
2004/0024311 A1 2/2004 Quaid, III
2004/0034282 A1 2/2004 Quaid
2004/0034283 A1 2/2004 Quaid
2004/0034302 A1 2/2004 Abovitz et al.
2004/0050394 A1 3/2004 Jin
2004/0070822 A1 4/2004 Takayama et al.
2004/0082952 A1 4/2004 Dycus et al.
2004/0099175 A1 5/2004 Perrot et al.
2004/0102772 A1 5/2004 Baxter et al.
2004/0106916 A1 6/2004 Quaid et al.
2004/0111113 A1 6/2004 Nakamura et al.
2004/0117032 A1 6/2004 Roth
2004/0138525 A1 7/2004 Saadat et al.
2004/0138552 A1 7/2004 Harel et al.
2004/0140786 A1 7/2004 Borenstein
2004/0153057 A1 8/2004 Davison
2004/0173116 A1 9/2004 Ghorbel et al.
2004/0176664 A1 9/2004 Iddan
2004/0215331 A1 10/2004 Chew et al.
2004/0225229 A1 11/2004 Viola
2004/0254680 A1 12/2004 Sunaoshi
2004/0267254 A1 12/2004 Manzo et al.
2004/0267326 A1 12/2004 Ocel et al.
2005/0014994 A1 1/2005 Fowler et al.
2005/0021069 A1 1/2005 Feuer et al.
2005/0029978 A1 2/2005 Oleynikov et al.
2005/0043583 A1 2/2005 Killmann et al.
2005/0049462 A1 3/2005 Kanazawa
2005/0054901 A1 3/2005 Yoshino
2005/0054902 A1 3/2005 Konno
2005/0064378 A1 3/2005 Toly
2005/0065400 A1 3/2005 Banik et al.
2005/0083460 A1 4/2005 Hattori et al.
2005/0095650 A1 5/2005 Julius et al.
2005/0096502 A1 5/2005 Khalili
2005/0143644 A1 6/2005 Gilad et al.
2005/0154376 A1 7/2005 Riviere et al.
2005/0165449 A1 7/2005 Cadeddu et al.
2005/0234435 A1 10/2005 Layer
2005/0239311 A1 10/2005 Yokoigawa et al.
2005/0283137 A1 12/2005 Doyle et al.
2005/0288555 A1 12/2005 Binmoeller
2005/0288665 A1 12/2005 Woloszko
2006/0020272 A1 1/2006 Gildenberg
2006/0046226 A1 3/2006 Bergler et al.
2006/0100501 A1 5/2006 Berkelman et al.
2006/0119304 A1 6/2006 Farritor et al.
2006/0149135 A1 7/2006 Paz
2006/0152591 A1 7/2006 Lin
2006/0155263 A1 7/2006 Lipow
2006/0195015 A1 8/2006 Mullick et al.
2006/0196301 A1 9/2006 Oleynikov et al.
2006/0198619 A1 9/2006 Oleynikov et al.
2006/0241570 A1 10/2006 Wilk
2006/0241732 A1 10/2006 Denker et al.
2006/0253109 A1 11/2006 Chu
2006/0258954 A1 11/2006 Timberlake et al.
2007/0032701 A1 2/2007 Fowler et al.
2007/0043397 A1 2/2007 Ocel et al.
2007/0055342 A1 3/2007 Wu et al.
2007/0080658 A1 4/2007 Farritor et al.
2007/0106113 A1 5/2007 Ravo
2007/0123748 A1 5/2007 Meglan
2007/0135803 A1 6/2007 Belson
2007/0142725 A1 6/2007 Hardin et al.
2007/0156019 A1 7/2007 Larkin et al.
2007/0156211 A1 7/2007 Wood et al.
2007/0167955 A1 7/2007 Arnault De La Menardiere et al.
2007/0225633 A1 9/2007 Wood et al.
2007/0225634 A1 9/2007 Wood et al.
2007/0241714 A1 10/2007 Okeynikov et al.
2007/0244520 A1 10/2007 Ferren et al.

(56) References Cited

U.S. PATENT DOCUMENTS

2007/0250064 A1 10/2007 Darois et al.
2007/0255273 A1 11/2007 Fernandez et al.
2008/0004634 A1 1/2008 Farritor et al.
2008/0015565 A1 1/2008 Davison
2008/0015566 A1 1/2008 Livneh
2008/0033569 A1 2/2008 Ferren et al.
2008/0039255 A1 2/2008 Jinno et al.
2008/0045803 A1 2/2008 Williams et al.
2008/0058835 A1 3/2008 Farritor et al.
2008/0058989 A1 3/2008 Oleynikov et al.
2008/0103440 A1 5/2008 Ferren et al.
2008/0109014 A1 5/2008 De La Pena
2008/0111513 A1 5/2008 Farritor et al.
2008/0119870 A1 5/2008 Williams
2008/0132890 A1 6/2008 Woloszko et al.
2008/0161804 A1 7/2008 Rioux et al.
2008/0164079 A1 7/2008 Jacobsen
2008/0183033 A1 7/2008 Bern et al.
2008/0221591 A1 9/2008 Farritor et al.
2008/0269557 A1 10/2008 Marescaux et al.
2008/0269562 A1 10/2008 Marescaux et al.
2009/0012532 A1 1/2009 Blackwell et al.
2009/0020724 A1 1/2009 Paffrath
2009/0024142 A1 1/2009 Ruiz Morales
2009/0048612 A1 2/2009 Farritor et al.
2009/0054909 A1 2/2009 Farritor et al.
2009/0069821 A1 3/2009 Farritor et al.
2009/0076536 A1 3/2009 Rentschler et al.
2009/0137952 A1 5/2009 Ramamurthy et al.
2009/0143787 A9 6/2009 De La Pena
2009/0163929 A1 6/2009 Yeung et al.
2009/0171373 A1 7/2009 Farritor et al.
2009/0209946 A1 8/2009 Kolata et al.
2009/0234369 A1 9/2009 Bax et al.
2009/0236400 A1 9/2009 Cole et al.
2009/0240246 A1 9/2009 Deville et al.
2009/0247821 A1 10/2009 Rogers
2009/0248038 A1 10/2009 Blumenkranz et al.
2009/0281377 A1 11/2009 Acosta et al.
2009/0287043 A1 11/2009 Naito et al.
2009/0305210 A1 12/2009 Guru et al.
2010/0010294 A1 1/2010 Conlon et al.
2010/0016659 A1 1/2010 Weitzner
2010/0016853 A1 1/2010 Burbank
2010/0042097 A1 2/2010 Newton et al.
2010/0056863 A1 3/2010 Dejima et al.
2010/0069710 A1 3/2010 Yamatani et al.
2010/0069940 A1 3/2010 Miller et al.
2010/0081875 A1 4/2010 Fowler et al.
2010/0139436 A1 6/2010 Kawashima et al.
2010/0179540 A1 7/2010 Marczyk et al.
2010/0185212 A1 7/2010 Sholev
2010/0198231 A1 8/2010 Scott
2010/0204713 A1 8/2010 Ruiz Morales
2010/0245549 A1 9/2010 Allen et al.
2010/0250000 A1 9/2010 Blumenkranz et al.
2010/0262162 A1 10/2010 Omori
2010/0286480 A1 11/2010 Peine et al.
2010/0292691 A1 11/2010 Brogna
2010/0312102 A1 12/2010 Barnes et al.
2010/0318059 A1 12/2010 Farritor et al.
2011/0015569 A1 1/2011 Kirschenman et al.
2011/0020779 A1 1/2011 Hannaford et al.
2011/0054462 A1 3/2011 Ellman
2011/0071347 A1 3/2011 Rogers et al.
2011/0071544 A1 3/2011 Steger et al.
2011/0077478 A1 3/2011 Freeman et al.
2011/0098529 A1 4/2011 Ostrovsky et al.
2011/0132960 A1 6/2011 Whitman et al.
2011/0152615 A1 6/2011 Schostek et al.
2011/0224605 A1 9/2011 Farritor et al.
2011/0230894 A1 9/2011 Simaan et al.
2011/0237890 A1 9/2011 Farritor et al.
2011/0238080 A1 9/2011 Ranjit et al.
2011/0245888 A1* 10/2011 Badelt .................. A61N 1/3931 607/6
2011/0264078 A1 10/2011 Lipow et al.
2011/0270443 A1 11/2011 Kamiya et al.
2011/0276046 A1 11/2011 Heimbecher et al.
2012/0029727 A1 2/2012 Malik
2012/0035582 A1 2/2012 Nelson et al.
2012/0109150 A1 5/2012 Blackwell et al.
2012/0116362 A1 5/2012 Kieturakis
2012/0179168 A1 7/2012 Farritor et al.
2012/0195078 A1 8/2012 Levin et al.
2012/0253515 A1 10/2012 Coste-Maniere et al.
2013/0041360 A1 2/2013 Farritor et al.
2013/0131695 A1 5/2013 Scarfogliero et al.
2013/0345717 A1 12/2013 Markvicka et al.
2014/0001234 A1 1/2014 Shelton, IV et al.
2014/0039515 A1 2/2014 Mondry et al.
2014/0046340 A1 2/2014 Wilson et al.
2014/0058205 A1 2/2014 Frederick et al.
2014/0249474 A1 9/2014 Suon et al.
2014/0303434 A1 10/2014 Farritor et al.
2014/0373652 A1 12/2014 Zergiebel et al.
2015/0051446 A1 2/2015 Farritor et al.
2015/0190170 A1 7/2015 Frederick et al.
2016/0143688 A1 5/2016 Orban, III et al.
2016/0291915 A1 10/2016 Panchapakesan et al.
2017/0258536 A1 9/2017 Yeung et al.
2018/0056527 A1 3/2018 Farritor et al.
2018/0140377 A1 5/2018 Reichenbach et al.
2019/0090965 A1 3/2019 Farritor et al.
2020/0170735 A1 6/2020 Yeung et al.
2020/0214775 A1 7/2020 Farritor et al.
2020/0281643 A1* 9/2020 Nussbaum ......... A61B 18/1206
2020/0305964 A1 10/2020 Brause et al.
2020/0352667 A1 11/2020 Kapadia et al.
2021/0045836 A1 2/2021 Farritor et al.
2021/0068913 A1 3/2021 Wang et al.
2021/0169592 A1 6/2021 Robinson et al.
2021/0290314 A1 9/2021 Sachs et al.
2021/0290323 A1 9/2021 Sachs et al.
2022/0000569 A1 1/2022 Farritor et al.

FOREIGN PATENT DOCUMENTS

CN 104224258 A 12/2014
DE 102010040405 A1 3/2012
EP 105656 A2 4/1984
EP 279591 A1 8/1988
EP 1354670 A1 10/2003
EP 1562504 B1 8/2005
EP 2286756 A1 2/2011
EP 2329787 A2 6/2011
EP 2563261 A1 3/2013
EP 2647339 A1 10/2013
EP 2684528 A1 1/2014
EP 2123225 B1 12/2014
EP 2815705 A1 12/2014
EP 2881046 A2 6/2015
EP 2937047 A1 10/2015
JP H04144533 A 5/1992
JP H05115425 A 5/1993
JP H05184535 A 7/1993
JP H06507809 A 9/1994
JP H06508049 A 9/1994
JP H07016235 A 1/1995
JP H07136173 A 5/1995
JP H07306155 A 11/1995
JP H08224248 A 9/1996
JP 2001500510 A 1/2001
JP 2001505810 A 5/2001
JP 2002000524 A 1/2002
JP 2003220065 A 8/2003
JP 2004180781 A 7/2004
JP 2004180858 A 7/2004
JP 2004322310 A 11/2004
JP 2004329292 A 11/2004
JP 2009106606 A 5/2009
JP 2010533045 A 10/2010
JP 2010536436 A 12/2010

(56) References Cited

FOREIGN PATENT DOCUMENTS

| | | | |
|---|---|---|---|
| JP | 2011504794 | A | 2/2011 |
| JP | 2011045500 | A | 3/2011 |
| JP | 2011115591 | A | 6/2011 |
| JP | 2017527392 | A | 9/2017 |
| KR | 20100029087 | A | 3/2010 |
| NO | 2013009887 | A1 | 1/2013 |
| WO | 9221291 | A2 | 12/1992 |
| WO | 9610957 | A1 | 4/1996 |
| WO | 9639944 | A1 | 12/1996 |
| WO | 0189405 | A1 | 11/2001 |
| WO | 02082979 | A2 | 10/2002 |
| WO | 02100256 | A2 | 12/2002 |
| WO | 2005009211 | A2 | 2/2005 |
| WO | 2005044095 | A1 | 5/2005 |
| WO | 2006005075 | A2 | 1/2006 |
| WO | 2006052927 | A2 | 5/2006 |
| WO | 2006079108 | A1 | 7/2006 |
| WO | 2007011654 | A1 | 1/2007 |
| WO | 2007111571 | A1 | 10/2007 |
| WO | 2007146987 | A2 | 12/2007 |
| WO | 2007149559 | A2 | 12/2007 |
| WO | 2009014917 | A2 | 1/2009 |
| WO | 2009023851 | A1 | 2/2009 |
| WO | 2009144729 | A1 | 12/2009 |
| WO | 2010042611 | A1 | 4/2010 |
| WO | 2010046823 | A1 | 4/2010 |
| WO | 2010050771 | A2 | 5/2010 |
| WO | 2011060311 | A2 | 5/2011 |
| WO | 2011075693 | A1 | 6/2011 |
| WO | 2011088387 | A2 | 7/2011 |
| WO | 2011118646 | A1 | 9/2011 |
| WO | 2011135503 | A1 | 11/2011 |
| WO | 2014011238 | A2 | 1/2014 |
| WO | 2015088655 | A1 | 6/2015 |
| WO | 2015152972 | A1 | 10/2015 |
| WO | 2019099903 | A1 | 5/2019 |
| WO | 2022248955 | A1 | 12/2022 |

OTHER PUBLICATIONS

Kantsevoy et al., "Endoscopic gastrojejunostomy with survival in a porcine model," Gastrointestinal Endoscopy, 2005; 62(2): 287-292.
Kantsevoy et al., "Transgastric endoscopic splenectomy," Surgical Endoscopy, 2006; 20: 522-525.
Kazemier et al. (1998), "Vascular Injuries During Laparoscopy," J. Am. Coli. Surg. 186(5): 604-5.
Keller et al., Design of the pediatric arm rehabilitation robot ChARMin, 2014, IEEE, p. 530-535 (Year: 2014).
Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136:180-184.
Leggett et al. (2002), "Aortic injury during laparoscopic fundoplication," Surg. Endoscopy 16(2): 362.
Li et al. (2000), "Microvascular Anastomoses Performed in Rats Using a Microsurgical Telemanipulator," Comp. Aid. Surg. 5: 326-332.
Liem et al., "Comparison of Conventional Anterior Surgery and Laparoscopic Surgery for Inguinal-hernia Repair," New England Journal of Medicine, 1997; 336 (22): 1541-1547.
Macfarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al., "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.
Menciassi et al., "Shape memory alloy clamping devices of a capsule for monitoring tasks in the gastrointestinal tract," J. Micromech. Microeng, 2005, 15: 2045-2055.
Meron, "The development of the swallowable video capsule (M2A)," Gastrointestinal Endoscopy 2000; 52 6: 817-819.
Micron, http://www.micron.com, 2006, ¼-inch VGA NTSC/PAL CMOS Digital Image Sensor, 98 pp.
Midday Jeff et al., "Material Handling System for Robotic natural Orifice Surgery", Proceedings of the 2011 Design of medical Devices Conference, Apr. 12-14, 2011, Minneapolis, MN, 4 pages.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 2004, 7 pp.
Munro (2002), "Laparoscopic access: complications, technologies, and techniques," Curro Opin. Obstel. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Oleynikov et al., "In Vivo Camera Robots Provide Improved Vision for Laparoscopic Surgery," Computer Assisted Radiology and Surgery (CARS), Chicago, IL, Jun. 23-26, 2004.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
O'Neill, "Surgeon takes new route to gallbladder," The Oregonian, Jun. 2007, 2 pp.
Orlando et al., (2003), "Needle and Trocar Injuries in Diagnostic Laparoscopy under Local Anesthesia: What Is the True Incidence of These Complications?" Journal of Laparoendoscopic & Advanced Surgical Techniques 13(3): 181-184.
Palm, William, "Rapid Prototyping Primer" May 1998 (revised Jul. 30, 2002) (http://www.me.psu.edu/lamancusa/rapidpro/primer/chapter2.htm).
Park et al., "Trocar-less Instrumentation for Laparoscopy: Magnetic Positioning of Intra-abdominal Camera and Retractor," Ann Surg, Mar. 2007; 245(3): 379-384.
Park et al., "Experimental studies of transgastric gallbladder surgery: cholecystectomy and cholecystogastric anastomosis (videos)," Gastrointestinal Endoscopy, 2005; 61(4): 601-606.
Patronik et al., "Development of a Tethered Epicardial Crawler for Minimally Invasive Cardiac Therapies," IEEE, 2004, pp. 239-240.
Patronik et al., "Crawling on the Heart: a Mobile Robotic Device for Minimally Invasive Cardiac Interventions," MICCAI, 2004, pp. 9-16.
Patronik et al., "Preliminary evaluation of a mobile robotic device for navigation and intervention on the beating heart," Computer Aided Surgery, 10(4): 225-232, Jul. 2005.
Peirs et al., "A miniature manipulator for integration in a self-propelling endoscope," Sensors and Actuators A, 2001, 92: 343-349.
Peters, "Minimally Invasive Colectomy: Are the Potential Benefits Realized?" Dis Colon Rectum 1993; 36: 751-756.
Phee et al., "Analysis and Development of Locomotion Devices for the Gastrointestinal Tract," IEEE Transaction on Biomedical Engineering, vol. 49, No. 6, Jun. 2002, pp. 613-616.
Phee et al., "Development of Microrobotic Devices for Locomotion in the Human Gastrointestinal Tract," International Conference on

(56) References Cited

OTHER PUBLICATIONS

Computational Intelligence, Robotics and Autonomous Systems (CIRAS 2001), Nov. 28-30, (2001), Singapore.
Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, FI. auderdale, FL, Apr. 13-16, 2005, 1 pg.
Rentschler et al., "Mobile In Vivo Biopsy and Camera Robot," Studies in Health and Infonnatics Medicine Meets Virtual Reality, vol. 119., pp. 449-454, IOS Press, Long Beach, CA, 2006.
Rentschler et al., "Mobile In Vivo Biopsy Robot," IEEE International Conference on Robotics and Automation, Orlando, Florida, May 2006, pp. 4155-4160.
Rentschler et al., "Miniature in vivo Robots for Remote and Harsh Environments," IEEE Transactions on Information Technology in Biomedicine. Jan. 2006; 12(1): 66-75.
Rentschler et al., "An In Vivo Mobile Robot for Surgical Vision and Task Assistance," Journal of Medical Devices, Mar. 2007, vol. 1: 23-29.
Rentschler et al., "In vivo Mobile Surgical Robotic Task Assistance," 1 pg.
Rentschler et al., "In vivo Robotics during the NEEMO 9 Mission," Medicine Meets Virtual Reality, Feb. 2007, 1 pg.
Rentschler et al., "In Vivo Robots for Laparoscopic Surgery," Studies in Health Technology and Infonnatics—Medicine Meets Virtual Reality, ISO Press, Newport Beach, CA, 2004a, 98: 316-322.
Rentschler et al., "Mechanical Design of Robotic In Vivo Wheeled Mobility," ASME Journal of Mechanical Design, 2006, pp. 1-11.
Rentschler et al., "Mobile In Vivo Camera Robots Provide Sole Visual Feedback for Abdominal Exploration and Cholecystectomy," Journal of Surgical Endoscopy, 20-1: 135-138, 2006b.
Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.
Rentschler et al., "Modeling, Analysis, and Experimental Study of In Vivo Wheeled Robotic Mobility," IEEE Transactions on Robotics, 22 (2): 308-321, 2005c.
Rentschler et al., "Natural Orifice Surgery with an Endoluminal Mobile Robot," The Society of American Gastrointestinal Endoscopic Surgeons, Dallas, TX, Apr. 2006d, 14 pp.
Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9.
Rentschler et al., "Toward In Vivo Mobility," Studies in Health Technology and Infonnatics—Medicine Meets Virtual Reality, ISO Press, Long Beach, CA, 2005a, III: 397-403.
Riviere et al., "Toward Active Tremor Canceling in Handheld Microsurgical Instruments," IEEE Transactions on Robotics and Automation, Oct. 2003, 19(5): 793-800.
Rosen et al., "Force Controlled and Teleoperated Endoscopic, Grasper for Minimally Invasive Surgery-Experimental Performance Evaluation," IEEE Transactions of Biomedical Engineering, Oct. 1999; 46(10): 1212-1221.
Rosen et al., "Objective Laparoscopic Skills Assessments of Surgical Residents Using Hidden Markov Models Based on Haptic Information and Tool/Tissue Interactions," Studies in Health Technology and Infonnatics-Medicine Meets Virtual Reality, Jan. 2001, 7 pp.
Rosen et al., "Spherical Mechanism Analysis of a Surgical Robot for Minimally Invasive Surgery—Analytical and Experimental Approaches," Studies in Health Technology and Infonnatics-Medicine Meets Virtual Reality, pp. 442-448, Jan. 2005.
Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.
Rosen et al., "The Blue DRAGON—a System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.
Ruurda et al., "Robot-Assisted surgical systems: a new era in laparoscopic surgery," Ann R. Coll Surg Engl., 2002; 84: 223-226.
Ruurda et al., "Feasibility of Robot-Assisted Laparoscopic Surgery," Surgical Laparoscopy, Endoscopy & Percutaneous Techniques, 2002; 12(1):41-45.
Sackier et al., "Robotically assisted laparoscopic surgery," Surgical Endoscopy, 1994; 8: 63-66.
Salky, "What is the Penetration of Endoscopic Techniques into Surgical Practice?" Digestive Surgery, 2000; 17:422-426.
Satava, "Surgical Robotics: the Early Chronicles," Surgical Laparoscopy, Endoscopy & Percutaneous Techniques, 2002; 12(1): 6-16.
Schippers et al., (1996) "Requirements and Possibilities of Computer-Assisted Endoscopic Surgery," In: Computer Integrated Surgery: Technology and Clinical Applications, pp. 561-565.
Schurr et al., "Robotics and Telemanipulation Technologies for Endoscopic Surgery," Surgical Endoscopy, 2000; 14: 375-381.
Schwartz, "In the Lab: Robots that Slink and Squirm," The New York Times, Mar. 27, 2007, 4 pp.
Sharp LL-151-3D, http://www.sharp3d.com, 2006, 2 pp.
Slatkin et al., "The Development of a Robotic Endoscope," Proceedings of the 1995 IEEE International Conference on Robotics and Automation, pp. 162-171, 1995.
Smart Pill "Fastastic Voyage: Smart Pill to Expand Testing," http://www.smartpilldiagnostics.com, Apr. 13, 2005, 1 pg.
Sodeyama et al., A shoulder structure of muscle-driven humanoid with shoulder blades, 2005, IEEE, p. 1-6 (Year: 2005).
Southern Surgeons Club (1991), "A prospective analysis of 1518 laparoscopic cholecystectomies," N. Eng. 1 Med. 324 (16): 1073-1078.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Stiff et al., "Long-term Pain: Less Common After Laparoscopic than Open Cholecystectomy," British Journal of Surgery, 1994; 81: 1368-1370.
Stoianovici et al., "Robotic Tools for Minimally Invasive Urologic Surgery", Jan. 1, 2002, pp. 1-17.
Strong et al., "Efficacy of Novel Robotic Camera vs. a Standard Laproscopic Camera," Surgical Innovation vol. 12, No. 4, Dec. 2005, Westminster Publications, Inc., pp. 315-318.
Suzumori et al., "Development of Flexible Microactuator and its Applications to Robotics Mechanisms," Proceedings of the IEEE International Conference on Robotics and Automation, 1991: 1622-1627.
Taylor et al., "A Telerobotic Assistant for Laparoscopic Surgery," IEEE Eng Med Biol, 1995; 279-287.
Tendick et al., (1993), "Sensing and Manipulation Problems in Endoscopic Surgery: Experiment, Analysis, and Observation," Presence 2(1): 66-81.
Tendick et al., "Applications of Micromechatronics in Minimally Invasive Surgery," IEEE/ASME Transactions on Mechatronics, 1998; 3(1): 34-42.
Thomann et al., "The Design of a new type of Micro Robot for the Intestinal Inspection," Proceedings of the 2002 IEEE Intl. Conference on Intelligent Robots and Systems, Oct. 2002: 1385-1390.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.

(56) References Cited

OTHER PUBLICATIONS

Way et al., (editors), "Fundamentals of Laparoscopic Surgery," Churchill Livingstone Inc., 1995, 14 pp.
Wolfe et al., "Endoscopic Cholecystectomy: an analysis of Complications," Arch. Surg. Oct. 1991; 126: 1192-1196.
Worn et al., "Espirit Project No. 33915: Miniaturised Robot for Micro Manipulation (MINIMAN)", Nov. 1998; http://www.ipr.ira.ujka.de/-microbol/miniman.
Yu et al., "Microrobotic Cell Injection," Proceedings of the 2001 IEEE International Conference on Robotics and Automation, May 2001; 620-625.
Yu, BSN, RN, "M2ATM Capsule Endoscopy a Breakthrough Diagnostic Tool for Small Intestine Imagining," vol. 25, No. 1, Gastroenterology Nursing, 2001, pp. 24-27.
Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
Abbou et al., "Laparoscopic Radical Prostatectomy with a Remote Controlled Robot," The Journal of Urology, Jun. 2001, 165: 1964-1966.
Albers et al., Design and development process of a humanoid robot upper body through experimentation, 2004, IEEE, p. 77-92 (Year: 2004).
Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon University, May 2004, 167 pp.
Atmel 80C5X2 Core, http://www.atmel.com, 2006, 186 pp.
Bailey et al., "Complications of Laparoscopic Surgery," Quality Medical Publishers, Inc., 1995, 25 pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 28-15.
Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.
Cavusoglu et al.," Robotics for Telesurgery: Second Generation Berkeley/UCSF Laparoscopic Telesurgical Workstation and Looking Towards the Future Applications," Industrial Robot: an International Journal, 2003; 30(1): 22-29.
Chanthasopeephan et al., (2003), "Measuring Forces in Liver Cutting: New Equipment and Experimental Results," Annals of Biomedical Engineering 31: 1372-1382.
Choi et al.,"Flexure-based Manipulator for Active Handheld Microsurgical Instrument," Proceedings of the 27th Annual International Conference of the IEEE Engineering in Medicine and Biology Society (EMBS), Sep. 2005, 4 pp.
Cleary et al., "State of the Art in Surgical Robotics: Clinical Applications and Technology Challenges", "Computer Aided Surgery", Jan. 1, 2002, pp. 312-328, vol. 6.
Cuschieri, "Technology for Minimal Access Surgery," BMJ, 1999, 319: 1-6.
Dakin et al., "Comparison of laparoscopic skills performance between standard instruments and two surgical robotic systems," Surg Endosc., 2003; 17: 574-579.
Dumpert et al., "Improving in Vivo Robot Vision Quality," from the Proceedings of Medicine Meets Virtual Reality, Long Beach, CA, Jan. 26-29, 2005. 1 pg.
Dumpert et al., "Stereoscopic In Vivo Surgical Robots," IEEE Sensors Special Issue on In Vivo Sensors for Medicine, Jan. 2007, 10 pp.
Falcone et al., "Robotic Surgery," Clin. Obstel. Gynecol. 2003, 46(1): 37-43.
Faraz et al., "Engineering Approaches to Mechanical and Robotic Design for Minimally Invasive Surgery (MIS)," Kluwer Academic Publishers (Boston), 2000, 13 pp.
Fearing et al., "Wing Transmission for a Micromechanical Flying Insect," Proceedings of the 2000 IEEE International Conference to Robotics & Automation, Apr. 2000; 1509-1516.
Fireman et al., "Diagnosing small bowel Crohn's disease with wireless capsule endoscopy," Gut 2003; 52: 390-392.
Flynn et al., "Tomorrow's Surgery: micromotors and microbots for minimally invasive procedures," Minimally Invasive Surgery & Allied Technologies, vol. 7, No. 4, 1998, pp. 343-352.
Franklin et al.,"Prospective Comparison of Open vs. Laparoscopic Colon Surgery for Carcinoma: Five-Year Results," Dis Colon Rectum, 1996; 39: S35-S46.
Franzino, "The Laprotek Surgical System and the Next Generation of Robotics," Surg Clin North Am, 2003 83(6), pp. 1317-1320.
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 EEE International Conference on Robotics and Automation, 1994: 814-819.
Fukuda et al., "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: a Report from a U.S. Food and Drug Administration (FDA) Center for Devices and Radiological Health (CDRH) Systematic Technology Assessment of Medical Products (STAMP) Committee," U.S. Food and Drug Adminstration, available at http://www.fdaJ:?;ov, Finalized: Nov. 7, 2003; Updated: Jun. 24, 2005, 11 pp.
Glukhovsky et al., "The development and application of wireless capsule endoscopy," Int. J. Med. Robot. Comput. Assisi. Surgery, 2004; I (1): 114-123.
Gong et al., "Wireless endoscopy," Gastrointestinal Endoscopy 2000; 51(6): 725-729.
Gopura et al., Mechanical designs of active upper-limb exoskeleton robots: State-of-the-art and design difficulties, 2009, IEEE, p. 178-187 (Year: 2009).
Grady, "Doctors Try New Surgery for Gallbladder Removal," The New York Times, Apr. 20, 2007, 3 pp.
Green, "Telepresence Surgery", Jan. 1, 1995, Publisher: IEEE Engineering in Medicine and Biology.
Guber et al., "Miniaturized Instrument Systems for Minimally Invasive Diagnosis and Therapy," Biomedizinishe Technic. 2002, Band 47, Erganmngsband 1.
Hanly et al., "Value of the SAGES Learning Center in introducing new technology," Surgical Endoscopy, 2004; 19(4): 477-483.
Hanly et al., "Robotic Abdominal Surgery," The American Journal of Surgery 188 (Suppl. to Oct. 1994): 19S-26S, 2004.
Heikkinen et al., "Comparison of laparoscopic and open Nissen fundoplication two years after operation: a prospective randomized trial," Surgical Endoscopy, 2000; 14: 1019-1023.
Hissink, "Olympus Medical develops capsule camera technology," Dec. 2004, accessed Aug. 29, 2007, http://www.letsgodigital.org , 3 pp.

(56) References Cited

OTHER PUBLICATIONS

Horgan et al., "Technical Report: Robots in Laparoscopic Surgery," Journal of Laparoendoscopic & Advanced Surgical Techniques, 2001; 11(6): 415-419.
Ishiyama et al., "Spiral-type Micro-machine for Medical Applications," 2000 International Symposium on Micromechatronics and Human Science, 2000: 65-69.
Jagannath et al., "Peroral transgastric endoscopic ligation of fallopian tubes with long-term survival in a porcine model," Gastrointestinal Endoscopy, 2005; 61(3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.
European Patent Office, "Extended European Search Report", From Application No. 23788876, Dated Feb. 23, 2026, pp. 9.

* cited by examiner

ENERGY COUPLING MITIGATION DEVICE AND RELATED SYSTEMS AND METHODS

CROSS-REFERENCE TO RELATED APPLICATION(S)

This application claims the benefit under 35 U.S.C. § 119(e) to U.S. Provisional Application 63/329,914, filed Apr. 12, 2022 and entitled "Energy Coupling Mitigation Device and Related Systems and Methods," which is hereby incorporated herein by reference in its entirety.

FIELD

The embodiments disclosed herein relate to various medical devices and related components that can make up a surgical system, including robotic and/or in vivo medical devices and related components. More specifically, the various devices and systems relate to robotic surgical devices for use in various surgical procedures, including laparoscopic surgery and the like.

BACKGROUND

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, CA) are also restricted by the access ports, as well as having the additional disadvantages of being very large, very expensive, unavailable in most hospitals, and having limited sensory and mobility capabilities.

Further, various devices require multiple elongate electrical conductors coupled thereto that transmit several types of electrical signals and different types of electrical power. Often a single sheath or casing is used to contain all of those conductors, resulting in a single cable. The use of such a cable reduces the number of separate exposed conductors and thereby reduces the risks of entanglements, etc. Because all of the conductors are in close proximity within and along the extended length of the cable, energy coupling can result in the transfer of electrical energy from one conductor to another. This can lead to excessive/unintended current flowing through conductors intended to be unenergized, especially those used for electrocautery and/or advanced energy electrosurgical devices or systems, which can result in inadvertent actuation of the wrong tools and/or end effectors of those devices/systems.

There is a need in the art for improved surgical methods, systems, and devices.

BRIEF SUMMARY

Discussed herein are various electrical disconnection systems or devices, including such systems or devices incorporated into various robotic surgical devices for mitigation or prevention of electrical current leakage.

In Example 1, a surgical system comprises at least one end effector, at least one conductor coupled to the end effector, and a disconnection mechanism associated with the at least one conductor, wherein the mechanism is configured to electrically disconnect the end effector from an energy source when not in use so as to reduce energy leakage out the instrument.

Example 2 relates to the surgical system according to Example 1, wherein the disconnection mechanism is configured to electrically disconnect the at least one conductor from the energy source.

Example 3 relates to the surgical system according to Example 1, wherein the disconnection mechanism is an electrical relay.

Example 4 relates to the surgical system according to Example 1, wherein the end effector is a bi-polar end effector.

Example 5 relates to the surgical system according to Example 1, wherein the end effector is a monopolar end effector.

Example 6 relates to the surgical system according to Example 1, wherein the at least one end effector comprises two end effectors.

Example 7 relates to the surgical system according to Example 1, wherein the end effector is an electrosurgical end effector.

Example 8 relates to the surgical system according to Example 1, further comprising an electrical current sensor coupled to the at least one conductor, wherein the electrical current sensor is disposed between the disconnection mechanism and the end effector.

Example 9 relates to the surgical system according to Example 8, wherein the electrical current sensor comprises a transformer current sensor, a Hall Effect current sensor, or a shunt resistor.

Example 10 relates to the surgical system according to Example 8, wherein a controller of the surgical system is operably coupled to the electrical current sensor, wherein the controller is configured to receive information from the electrical current sensor and modulate energy delivery from the energy source to the end effector based on the information from the electrical current sensor.

Example 11 relates to the surgical system according to Example 10, wherein the controller is configured to shut down the energy source when a disconnection mechanism failure is detected at the electrical current sensor.

In Example 12, a robotic surgical device comprises an elongate device body, a first robotic arm operably coupled to the elongate device body, the first robotic arm comprising a first end effector operably coupled to the first robotic arm and a first conductor coupled to the first end effector. The first conductor comprises a proximal length disposed within the elongate device body and extending out of a proximal portion of the device body to an external energy source, and a distal length disposed within the elongate device body and extending out of a distal portion of the device body and through the first robotic arm to the first end effector. Further the robotic surgical device further comprises a disconnection mechanism disposed within the elongate device body and coupled with the proximal length and the distal length of the first conductor, wherein the disconnection mechanism comprises a switch comprising an open position and a closed position.

Example 13 relates to the robotic surgical device according to Example 12, wherein, when the switch is in the open position, the distal length is electrically disconnected from the proximal length of the first conductor.

Example 14 relates to the robotic surgical device according to Example 12, wherein the disconnection mechanism is an electrical relay.

Example 15 relates to the robotic surgical device according to Example 12, wherein the first end effector is a bi-polar end effector or a monopolar end effector.

Example 16 relates to the robotic surgical device according to Example 12, further comprising an electrical current sensor coupled to the distal length of the first conductor.

Example 17 relates to the robotic surgical device according to Example 16, wherein a controller of the surgical system is operably coupled to the electrical current sensor, wherein the controller is configured to receive information from the electrical current sensor and modulate energy delivery from the external energy source to the first end effector based on the information from the electrical current sensor.

Example 18 relates to the robotic surgical device according to Example 17, wherein the controller is configured to shut down the external energy source when a disconnection mechanism failure is detected at the electrical current sensor.

Example 19 relates to the robotic surgical device according to Example 12, further comprising a second robotic arm operably coupled to the elongate device body, the second robotic arm comprising a second end effector operably coupled to the second robotic arm.

In Example 20, a method of mitigating energy coupling during use of a robotic surgical device comprises positioning the robotic surgical device within a patient cavity, the robotic surgical device comprising an elongate device body, a first robotic arm operably coupled to the elongate device body, the first robotic arm comprising a first end effector operably coupled to the first robotic arm, a first conductor extending through the elongate device body and the first robotic arm and coupled to the first end effector, a disconnection mechanism disposed within the elongate device body and coupled with the first conductor, a second robotic arm operably coupled to the elongate device body, the second robotic arm comprising a second end effector operably coupled to the second robotic arm, and a second conductor extending through the elongate device body and the second robotic arm and coupled to the second end effector, whereby the elongate device body is disposed through an incision into the patient cavity and the first robotic arm is disposed within the patient cavity. The method further comprises actuating the disconnection mechanism to disconnect a proximal end of the first conductor from a distal end of the first conductor when the second end effector is actuated and actuating the disconnection mechanism to connect the proximal end of the first conductor to the distal end of the first conductor when the first end effector is actuated.

While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

DETAILED DESCRIPTION

Figure 1:
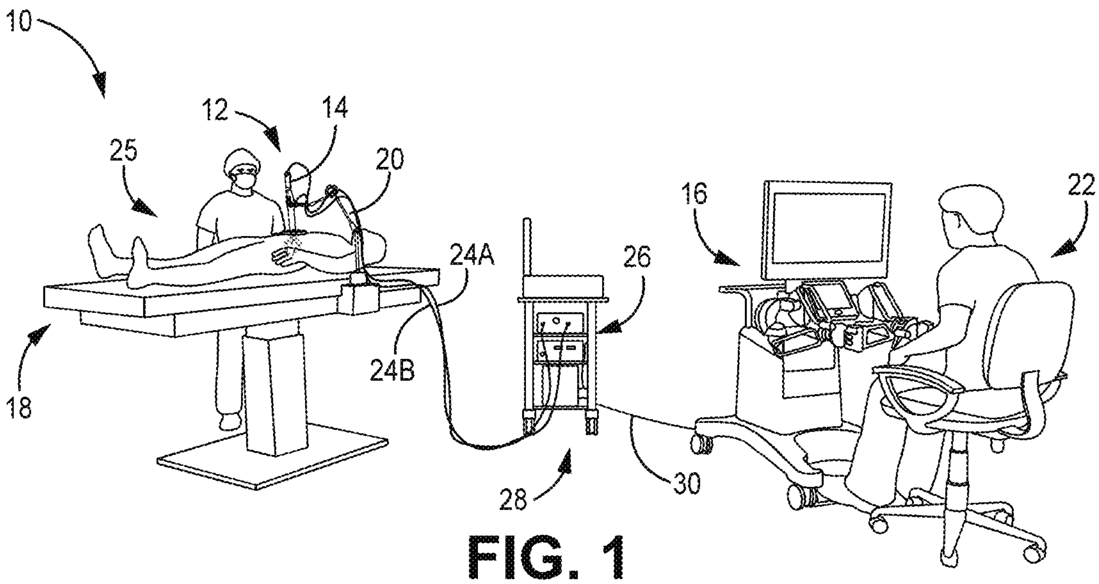
FIG. 1 is a perspective view of a robotic surgical system in an operating room, according to one embodiment.

The various systems and devices disclosed herein relate to devices for use in medical procedures and systems. More specifically, various embodiments relate to various medical devices and related methods and systems having specific devices or systems for preventing or reducing the transfer of electrical energy between conductors within the devices, thereby reducing or eliminating excessive and/or unintentional electrical current flowing through conductors intended to be unenergized (have no electrical current flowing therethrough) during certain operational modes. For purposes of this application, a conductor intended to have no electrical current flowing therethrough in certain operational modes (typically because the end effector coupled thereto is not intended to be actuated in those specific modes) is also referred to herein as "quiescent conductor.".

It is understood that the various embodiments of robotic devices and related methods and systems disclosed herein, including the devices or systems for prevention or reduction of unintentional electrical energy transfer, can be incorporated into or used with any other known medical devices, systems, and methods.

It is understood that the various embodiments of robotic devices and related methods and systems disclosed herein can be incorporated into or used with any other known medical devices, systems, and methods. For example, the various embodiments disclosed herein may be incorporated into or used with any of the medical devices and systems disclosed in U.S. Pat. No. 8,968,332 (issued on Mar. 3, 2015 and entitled "Magnetically Coupleable Robotic Devices and Related Methods"), U.S. Pat. No. 8,834,488 (issued on Sep. 16, 2014 and entitled "Magnetically Coupleable Surgical Robotic Devices and Related Methods"), U.S. Pat. No. 10,307,199 (issued on Jun. 4, 2019 and entitled "Robotic Surgical Devices and Related Methods"), U.S. Pat. No. 9,579,088 (issued on Feb. 28, 2017 and entitled "Methods, Systems, and Devices for Surgical Visualization and Device Manipulation"), U.S. Patent Application 61/030,588 (filed on Feb. 22, 2008), U.S. Pat. No. 8,343,171 (issued on Jan. 1, 2013 and entitled "Methods and Systems of Actuation in Robotic Devices"), U.S. Pat. No. 8,828,024 (issued on Sep. 9, 2014 and entitled "Methods and Systems of Actuation in Robotic Devices"), U.S. Pat. No. 9,956,043 (issued on May 1, 2018 and entitled "Methods and Systems of Actuation in Robotic Devices"), U.S. patent application Ser. No. 15/966,606 (filed on Apr. 30, 2018 and entitled "Methods, Systems, and Devices for Surgical Access and Procedures"), U.S. patent application Ser. No. 12/192,663 (filed on Aug. 15, 2008 and entitled "Medical Inflation, Attachment, and Delivery Devices and Related Methods"), U.S. patent application Ser. No. 15/018,530 (filed on Feb. 8, 2016 and entitled "Medical Inflation, Attachment, and Delivery Devices and Related Methods"), U.S. Pat. No. 8,974,440 (issued on Mar. 10, 2015 and entitled "Modular and Cooperative Medical Devices and Related Systems and Methods"), U.S. Pat. No. 8,679,096 (issued on Mar. 25, 2014 and entitled "Multifunctional Operational Component for Robotic Devices"), U.S. Pat. No. 9,179,981 (issued on Nov. 10, 2015 and entitled "Multifunctional Operational Component for Robotic Devices"), U.S. Pat. No. 9,883,911 (issued on Feb. 6, 2018 and entitled "Multifunctional Operational Component for Robotic Devices"), U.S. patent application Ser. No. 15/888,723 (filed on Feb. 5, 2018 and entitled "Multifunctional Operational Component for Robotic Devices"), U.S. Pat. No. 8,894,633 (issued on Nov. 25, 2014 and entitled "Modular and Cooperative Medical Devices and Related Systems and Methods"), U.S. Pat. No. 8,968,267 (issued on Mar. 3, 2015 and entitled "Methods and Systems for Handling or Delivering Materials for Natural Orifice Surgery"), U.S. Pat. No. 9,060,781 (issued on Jun. 23, 2015 and entitled "Methods, Systems, and Devices Relating to Surgical End Effectors"), U.S. Pat. No. 9,757,187 (issued on Sep. 12, 2017 and entitled "Methods, Systems, and Devices Relating to Surgical End Effectors"), U.S. Pat. No. 10,350,000 (issued on Jul. 16, 2019 and entitled "Methods, systems, and devices relating to surgical end effectors"), U.S. patent application Ser. No. 16/512,510 (filed on Jul. 16, 2019 and entitled "Methods, Systems, and Devices Relating to Surgical End Effectors"), U.S. Pat. No. 9,089,353 (issued on Jul. 28, 2015 and entitled "Robotic Surgical Devices, Systems, and Related Methods"), U.S. Pat. No. 10,111,711 (issued on Oct. 30, 2018 and entitled "Robotic Surgical Devices, Systems, and Related Methods"), U.S. patent application Ser. No. 16/123,619 (filed on Sep. 6, 2018 and entitled "Robotic Surgical Devices, Systems and Related Methods"), U.S. Pat. No. 9,770,305 (issued on Sep. 26, 2017 and entitled "Robotic Surgical Devices, Systems, and Related Methods"), U.S. patent application Ser. No. 15/661,147 (filed on Jul. 27, 2017 and entitled "Robotic Devices with On Board Control & Related Systems & Devices"), U.S. patent application Ser. No. 13/833,605 (filed on Mar. 15, 2013 and entitled "Robotic Surgical Devices, Systems, and Related Methods"), U.S. patent application Ser. No. 13/738,706 (filed on Jan. 10, 2013 and entitled "Methods, Systems, and Devices for Surgical Access and Insertion"), U.S. patent application Ser. No. 14/661,465 (filed on Mar. 18, 2015 and entitled "Methods, Systems, and Devices for Surgical Access and Insertion"), U.S. patent application Ser. No. 15/890,860 (filed on Feb. 7, 2018 and entitled "Methods, Systems, and Devices for Surgical Access and Insertion"), U.S. Pat. No. 9,498,292 (issued on Nov. 22, 2016 and entitled "Single Site Robotic Devices and Related Systems and Methods"), U.S. Pat. No. 10,219,870 (issued on Mar. 5, 2019 and entitled "Single site robotic device and related systems and methods"), U.S. patent application Ser. No. 16/293,135 (filed Mar. 3, 2019 and entitled "Single Site Robotic Device and Related Systems and Methods"), U.S. Pat. No. 9,010,214 (issued on Apr. 21, 2015 and entitled "Local Control Robotic Surgical Devices and Related Methods"), U.S. Pat. No. 10,470,828 (issued on Nov. 12, 2019 and entitled "Local Control Robotic Surgical Devices and Related Methods"), U.S. patent application Ser. No. 16/596,034 (filed on Oct. 8, 2019 and entitled "Local Control Robotic Surgical Devices and Related Methods"), U.S. Pat. No. 9,743,987 (issued on Aug. 29, 2017 and entitled "Methods, Systems, and Devices Relating to Robotic Surgical Devices, End Effectors, and Controllers"), U.S. patent application Ser. No. 15/687,787 (filed on Aug. 28, 2017 and entitled "Methods, Systems, and Devices Relating to Robotic Surgical Devices, End Effectors, and Controllers"), U.S. Pat. No. 9,888,966 (issued on Feb. 13, 2018 and entitled "Methods, Systems, and Devices Relating to Force Control Surgical Systems"), U.S. patent application Ser. No. 15/894,489 (filed on Feb. 12, 2018 and entitled "Methods, Systems, and Devices Relating to Force Control Surgical Systems"), U.S. patent application Ser. No. 14/212,686 (filed on Mar. 14, 2014 and entitled "Robotic Surgical Devices, Systems, and Related Methods"), U.S. patent application Ser. No. 14/334,383 (filed on Jul. 17, 2014 and entitled "Robotic Surgical Devices, Systems, and Related Methods"), U.S. patent application Ser. No. 14/853,477 (filed on Sep. 14, 2015 and entitled "Quick-Release End Effectors and Related Systems and Methods"), U.S. patent application Ser. No. 16/504,793 (filed on Jul. 8, 2019 and entitled "Quick-Release End Effectors and Related Systems and Methods"), U.S. Pat. No. 10,376,322 (issued on Aug. 13, 2019 and entitled "Robotic Device with Compact Joint Design and Related Systems and Methods"), U.S. patent application Ser. No. 16/538,902 (filed on Aug. 13, 2019 and entitled "Robotic Device with Compact Joint Design and Related Systems and Methods"), U.S. patent application Ser. No. 15/227,813 (filed on Aug. 3, 2016 and entitled Robotic Surgical Devices, System and Related Methods") U.S. patent application Ser. No. 15/599,231 (filed on May 18, 2017 and entitled "Robotic Surgical Devices, Systems, and Related Methods"), U.S. patent application Ser. No. 15/687,113 (filed on Aug. 25, 2017 and entitled "Quick-Release End Effector Tool Interface"), U.S. patent application Ser. No. 15/691,087 (filed on Aug. 30, 2017 and entitled "Robotic Device with Compact Joint Design and an Additional Degree of Freedom and Related Systems and Methods"), U.S. patent application Ser. No. 15/821,169 (filed on Nov. 22, 2017 and entitled "Gross Positioning Device and Related Systems and Methods"), U.S. patent application Ser. No. 15/826,166 (filed on Nov. 29, 2017 and entitled "User controller with user presence detection and related systems and methods"), U.S. patent application Ser. No. 15/842,230 (filed on Dec. 14, 2017 and entitled "Releasable Attachment Device for Coupling to Medical Devices and Related Systems and Methods"), U.S. patent application Ser. No. 16/144,807 (filed on Sep. 27, 2018 and entitled "Robotic Surgical Devices with Tracking Camera Technology and Related Systems and Methods"), U.S. patent application Ser. No. 16/241,263 (filed on Jan. 7, 2019 and entitled "Single-Manipulator Robotic Device With Compact Joint Design and Related Systems and Methods"), U.S. Pat. No. 7,492, 116 (filed on Oct. 31, 2007 and entitled "Robot for Surgical applications"), U.S. Pat. No. 7,772,796 (filed on Apr. 3, 2007 and entitled "Robot for Surgical applications"), U.S. Pat. No. 8,179,073 (issued on May 15, 2011, and entitled "Robotic Devices with Agent Delivery Components and Related Methods"), and U.S. patent application Ser. No. 16/736,329 (filed on Jan. 7, 2020 and entitled Robotically Assisted Surgical System and Related Devices and Methods), all of which are hereby incorporated herein by reference in their entireties.

Further, the various embodiments disclosed herein may be incorporated into or used with any other known electrosurgical medical devices and systems, including, for example, those disclosed in U.S. Pat. Nos. 9,427,282, 11,166,758, U.S. Published Application 2021/0169592, U.S. Published Application 2021/0290314, U.S. Published Application 2021/0290323, U.S. Published Application 2021/0068913, and U.S. Published Application 2011/0054462.

Certain device and system implementations disclosed in the applications listed above can be positioned within a body cavity of a patient, or a portion of the device can be placed within the body cavity, in combination with a support component similar to those disclosed herein. An "in vivo device" as used herein means any device that can be positioned, operated, or controlled at least in part by a user while being positioned within a body cavity of a patient, including any device that is coupled to a support component such as a rod or other such component that is disposed through an opening or orifice of the body cavity, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain embodiments provide for insertion of the various devices herein into the cavity while maintaining sufficient insufflation of the cavity. Further embodiments minimize the physical contact of the surgeon or surgical users with the device during the insertion process. Other implementations enhance the safety of the insertion process for the patient and the various embodiments herein. For example, some embodiments provide visualization of the device as it is being inserted into the patient's cavity to ensure that no damaging contact occurs between the system/device and the patient. In addition, certain embodiments allow for minimization of the incision size/length. Other implementations include devices that can be inserted into the body via an incision or a natural orifice. Further implementations reduce the complexity of the access/insertion procedure and/or the steps required for the procedure. Other embodiments relate to devices that have minimal profiles, minimal size, or are generally minimal in function and appearance to enhance ease of handling and use.

As in manual laparoscopic procedures, a known insufflation system can be used to pump sterile carbon dioxide (or other gas) into the patient's abdominal cavity. This lifts the abdominal wall from the organs and creates space for the robot. In certain implementations, the system has no direct interface with the insufflation system. Alternatively, the system can have a direct interface to the insufflation system.

In certain implementations in which the device is inserted through an insertion port, the insertion port is a known, commercially-available flexible membrane placed transabdominally to seal and protect the abdominal incision. This off-the-shelf component is the same device or substantially the same device that is used in substantially the same way for Hand-Assisted Laparoscopic Surgery (HALS). The only difference is that the arms of the robotic device according to the various embodiments herein are inserted into the abdominal cavity through the insertion port rather than the surgeon's hand. The robotic device body seals against the insertion port when it is positioned therethrough, thereby maintaining insufflation pressure. The port is single-use and disposable. Alternatively, any known port can be used. In further alternatives, the device can be inserted through an incision without a port or through a natural orifice.

Certain implementations disclosed herein relate to "combination" or "modular" medical devices that can be assembled in a variety of configurations. For purposes of this application, both "combination device" and "modular device" shall mean any medical device having modular or interchangeable components that can be arranged in a variety of different configurations.

Certain embodiments disclosed or contemplated herein can be used for colon resection, a surgical procedure performed to treat patients with lower gastrointestinal diseases such as diverticulitis, Crohn's disease, inflammatory bowel disease and colon cancer. Approximately two-thirds of known colon resection procedures are performed via a completely open surgical procedure involving an 8- to 12-inch incision and up to six weeks of recovery time. Because of the complicated nature of the procedure, existing robot-assisted surgical devices are rarely used for colon resection surgeries, and manual laparoscopic approaches are only used in one-third of cases. In contrast, the various implementations disclosed herein can be used in a minimally invasive approach to a variety of procedures that are typically performed 'open' by known technologies, with the potential to improve clinical outcomes and health care costs. Further, the various implementations disclosed herein can be used for any laparoscopic surgical procedure in place of the known mainframe-like laparoscopic surgical robots that reach into the body from outside the patient. That is, the less-invasive robotic systems, methods, and devices disclosed herein feature small, self-contained surgical devices that are inserted in their entireties through a single incision in the patient's abdomen. Designed to utilize existing tools and techniques familiar to surgeons, the devices disclosed herein will not require a dedicated operating room or specialized infrastructure, and, because of their much smaller size, are expected to be significantly less expensive than existing robotic alternatives for laparoscopic surgery. Due to these technological advances, the various embodiments herein could enable a minimally invasive approach to procedures performed in open surgery today.

FIG. 1 depicts one embodiment of a robotic surgical system 10 having several components that will be described in additional detail below. The components of the various system implementations disclosed or contemplated herein can include an external control console 16 and a robotic device 12 having a removable camera 14 as will also be described in additional detail below. In accordance with the implementation of FIG. 1, the robotic device 12 is shown mounted to the operating table 18 via a known, commercially available support arm 20. The system 10 can be, in certain implementations, operated by the surgeon 22 at the console 16 and one surgical assistant 25 positioned at the operating table 18. Alternatively, one surgeon 22 can operate the entire system 10. In a further alternative, three or more people can be involved in the operation of the system 10. It is further understood that the surgeon (or user) 22 can be located at a remote location in relation to the operating table 18 such that the surgeon 22 can be in a different city or country or on a different continent from the patient on the operating table 18.

Figure 2:
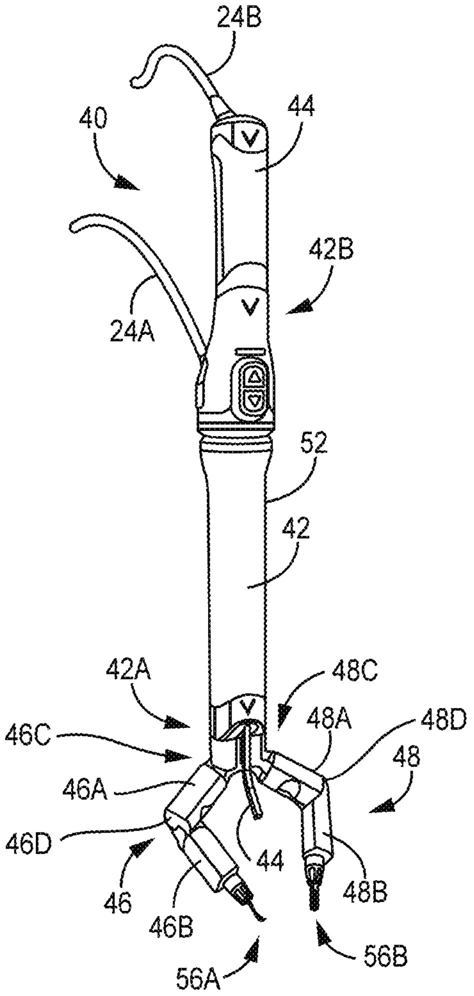
FIG. 2 is perspective view of a robotic device, according to one embodiment.

In this specific implementation, the robotic device 12 with the camera 14 are both connected to the surgeon console 16 via cables: a device cable 24A and a camera cable 24B that will be described in additional detail below. For purposes of this application, the term "cable" is intended to mean any sheath or elongate casing that can contain two or more different elongate cables, wires, and/or cords (referred to herein as "conductors"). In the specific embodiment as shown in FIGS. 1-2, the device 12 and camera 14 are connected to the surgeon console 16 via the device cable 24A and the camera cable 24B, which are coupled to an interface pod and electrosurgical unit 26 (which can be mounted in certain embodiments on a companion cart 28), and the pod and surgical unit 26 are coupled to the console 16 via a separate cable 30. According to one implementation, the device cable 24A is fixedly attached to the device 12 and can extend several feet to the pod and surgical unit 26. The cable 24A can be bifurcated near its proximal end so that robot signal/power conductors (discussed below) can connect to the interface pod 26 and the electrosurgical conductors can attach to the electrosurgical unit 26. Alternatively, these could also be combined into one connector on a cable that does not bifurcate. Alternatively, any connection configuration can be used. In certain implementations, the system can also interact with other devices during use such as a electrosurgical generator, an insertion port, and auxiliary monitors.

FIG. 2 depicts one exemplary implementation of a robotic device 40 that can be incorporated into the exemplary system 10 discussed above or any other system disclosed or contemplated herein. The device 40 has a body (or "torso") 42 having a distal end 42A and proximal end 42B, with the imaging device (or "camera") 44 disposed therethrough, as mentioned above and as will be described in additional detail below. Briefly, the robotic device 40 has two robotic arms 46, 48 operably coupled thereto and the camera 44 is removably positionable through the body 42 such that the distal end of the camera 44 is disposed between the two arms 46, 48. That is, device 40 has a first (or "right") arm 46 and a second (or "left") arm 48, both of which are operably coupled to the device 40 as discussed in additional detail below. In this embodiment, the body 42 of the device 40 as shown has an enclosure (also referred to as a "cover" or "casing") 52 such that the internal components and lumens of the body 42 are disposed within the enclosure 52. Each arm 46, 48 in this implementation also has an upper arm (also referred to herein as an "inner arm," "inner arm assembly," "inner link," "inner link assembly," "upper arm assembly," "first link," or "first link assembly") 46A, 48A, and a forearm (also referred to herein as an "outer arm," "outer arm assembly," "outer link," "outer link assembly," "forearm assembly," "second link," or "second link assembly") 46B, 48B. The right upper arm 46A is operably coupled to the body 42 at the right shoulder joint 46C and the left upper arm 48A is operably coupled to the body 42 at the left shoulder joint 48C. The shoulder joints 46C, 48C can be any known shoulder joints 46C, 48C of any configuration for rotatably attaching the arms 46, 48 to the body 42. Further, for each arm 46, 48, the forearm 46B, 48B is rotatably coupled to the upper arm 46A, 48A at the elbow joint 46D, 48D. In various embodiments, the forearms 46B, 48B are configured to receive various removeable, interchangeable end effectors 56A, 56B. Alternatively, each arm 46, 48 can be a single, unitary arm without an elbow joint, with the end effectors 56A, 56B disposed at the distal end of the unitary arms 46, 48. For purposes of this application, an "end effector" is any operational component, tool, instrument, or other device that is coupleable to a surgical device or system (including a robotic surgical device or system) and configured to interact with the environment, wherein such interaction can include performing a task or procedure.

The end effectors 56A, 56B on the distal end of the arms 46, 48 can be various tools 56A, 56B (scissors, graspers, needle drivers and the like), as will be described in additional detail below. In certain implementations, the tools 56A, 56B are designed to be removable, including in some instances by a small twist of the tool knob that couples the end effector 56A, 56B to the arm 46, 48. In certain implementations, at least two single-use, interchangeable, disposable surgical end effectors can be used with any of the robotic device embodiments herein (including device 40). Such end effectors can include, but are not limited to, a fenestrated grasper capable of bi-polar cautery, scissors that deliver mono-polar cautery, a hook that delivers mono-polar cautery, and a left/right needle driver set. The tools can be selected for the specific surgical task. Certain forearm and end effector configurations that allow for the removability and interchangeability of the end effectors are disclosed in detail in U.S. application Ser. No. 14/853,477, which is incorporated by reference above. Further, it is understood that any known forearm and end effector combinations can be used in any of the robotic device embodiments disclosed or contemplated herein.

In some embodiments, at least one of the two end effectors 56A, 56B is a cauterization device, such as a monopolar cauterization device or a bi-polar cauterization device. In this exemplary implementation as shown in FIG. 2, the right end effector 56A is a scissors that is a monopolar cauterization device 56A and the left end effector 56B is a fenestrated grasper that is a bi-polar cauterization device 56B. Alternatively, many energy/cauterization device configurations are possible. It is also possible to deliver two or more types of energy through a single cauterization end effector.

In various implementations, the body 40 and each of the links of the arms 46, 48 can contain a variety of actuators or motors. In certain implementations, the body 40 has no motors disposed therein, while there is at least one motor in each of the arms 46, 48. In one embodiment, any of the motors discussed and depicted herein can be brush or brushless motors. Further, the motors can be, for example, 6 mm, 8 mm, or 10 mm diameter motors. Alternatively, any known size that can be integrated into a medical device can be used. In a further alternative, the actuators can be any known actuators, including any known motors, used in medical devices to actuate movement or action of a component. Examples of motors that could be used in the embodiments herein include the EC 10 BLDC+GP10A Planetary Gearhead, EC 8 BLDC+GP8A Planetary Gearhead, or EC 6 BLDC+GP6A Planetary Gearhead, all of which are commercially available from Maxon Motors, located in Fall River, MA. There are many ways to actuate these motions electrically, such as with DC motors, AC motors, permanent magnet DC motors, brushless motors, cables to remote motors, and the like. As such, the actuation source can be at least one motor or any other electrical actuation source disposed remotely from or proximally to the device 40 such that an appropriate coupling or transmission mechanism (such as at least one cable or any other electrical transmission mechanism) is disposed through the body 42.

In one embodiment, the various joints discussed above in accordance with any of the embodiments disclosed or contemplated herein can be driven by electrical motors disposed within the device and, in some implementations, near each joint. In additional alternative embodiments, the driving actuators are disposed outside the device and/or body cavity and electrical transmission mechanisms are provided to transmit the electrical energy from the external source to the various joints of any device herein. Such a transmission mechanism could, for example, take the form of cables or other known electrical mechanisms, or any combination thereof.

In accordance with one implementation, FIG. 2 also depicts the device cable 24A and the camera cable 24B discussed above, with the device cable 24A extending from the device body 42 and the camera cable 24B extending from the camera 44 as shown. According to various embodiments, the device cable 24A is a single cable 24A containing all the necessary separate elongate conductors for transmission of all electrical signals and power as discussed above. A single elongate device cable 24A can be desirable, because it can simplify set up and handling of the device 40 and system 10 without having to deal with numerous separate cables/conductors/etc. In this specific implementation, the cable 24A is permanently connected to the robot 40 and is removably coupleable to the interface pod 26 via an electrical connector (not shown). Alternatively, any connection is possible at either end of the cable 24A.

Figure 3A:
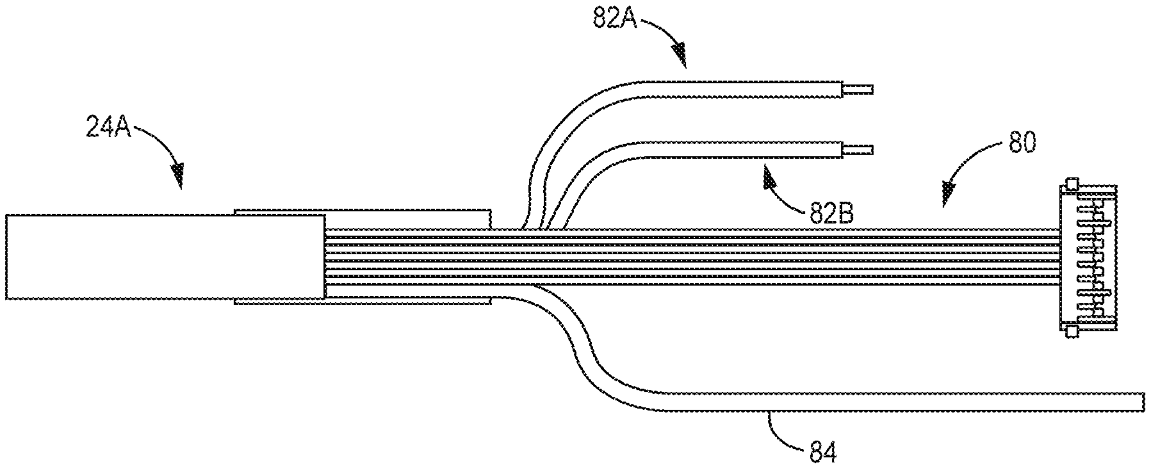
FIG. 3A is an expanded side view of a device cable and the conductors contained therein, according to one embodiment.
Figure 3B:
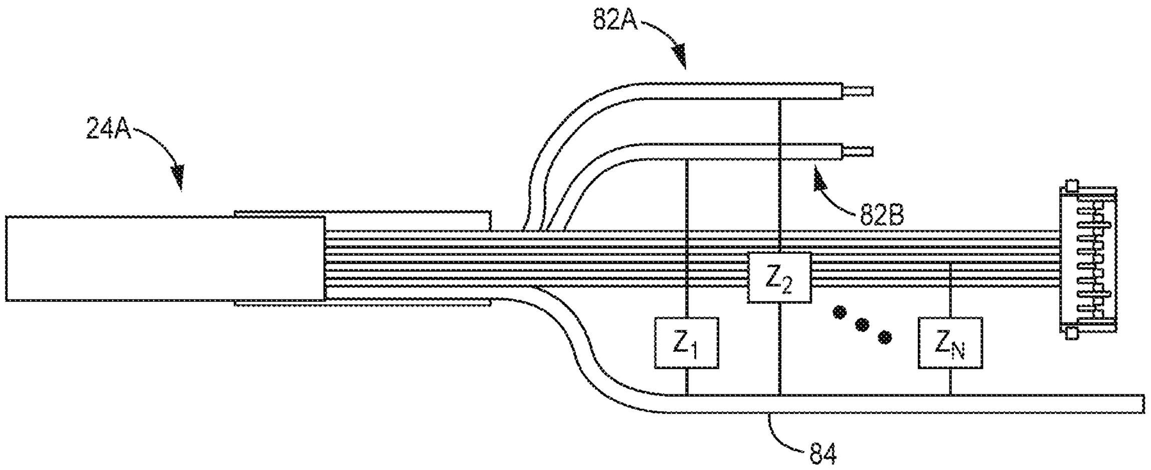
FIG. 3B is an expanded side view of the device cable and conductors of FIG. 3A with energy coupling, according to one embodiment.

An exploded view of one exemplary device cable 24A is depicted in FIGS. 3A and 3B according to one embodiment, in which the cable 24A contains several conductors that transmit several types of electrical signals and different types of electrical power. For example, several of the conductors 80 transmit power and digital/analog signals that are used to power the motion of the robotic device 40 and to send signals (in one specific implementation, a version of RS-485 is used) to control the motion of the device 40. In addition, the device cable 24A also contains a pair of conductors 82A, 82B (which are typically twisted around each other along the length of the cable 24A) for transmission of bi-polar electrosurgical energy to any bi-polar cauterization end effector that may be coupled to either or both of the arms 46, 48. Further, the cable 24A has an elongate conductor 84 (in certain embodiments, a co-axial cable) that provides transmission of mono-polar energy to any mono-polar cauterization end effector that may be coupled to either or both arms 46, 48. Alternatively, the cable 24A can contain any combination of conductors necessary to provide appropriate electrical signals and power to a robotic surgical device such as device 40.

As discussed above, because all of the various elongate conductors within the single device cable 24A (including the conductors 82A, 82B and conductor 84) are in close proximity within and along the extended length of the cable 24A, some energy coupling exists between each pair of conductors within the cable 24A. For example, this energy coupling can be capacitance or inductance that can be envisioned as an impedance between each pair of conductors, shown schematically in FIG. 3B. Alternatively, any known form of energy coupling can result. In this schematic depiction, the coupling is shown as Zn between any pair of conductors. This energy coupling can result in the transfer of electrical energy from one conductor/cord to another.

Because of the possibility of electrical energy transferring to a quiescent conductor, the energy couplings Z1 and Z2 between the mono-polar conductor 84 and bi-polar conductors 82A, 82B as shown in FIG. 3B are of particular interest within the context of the various embodiments herein. That is, both the mono-polar conductor 84 and bi-polar conductors 82A, 82B carry relatively high voltage, high frequency electrical energy, which increases the possibility of transferring electrical energy therebetween. Further, because the mono-polar conductor 84 is connected to a mono-polar cauterization end effector (such as end effector 56A) and the bi-polar conductors 82A, 82B are connected to a bi-polar cauterization end effector (such as end effector 56B), any energy transferred from one conductor to the other (such as from the monopolar elongate conductor 84 to the bi-polar elongate conductors 82A, 82B) can be directly transmitted to the unintended end effector and thus to the target surgical tissue, thereby risking serious injury to the patient. (In contrast, transfer of energy to any of the other conductors is of little concern, because those conductors have no direct path to an end effector and/or the target surgical tissue.)

Figure 4A:
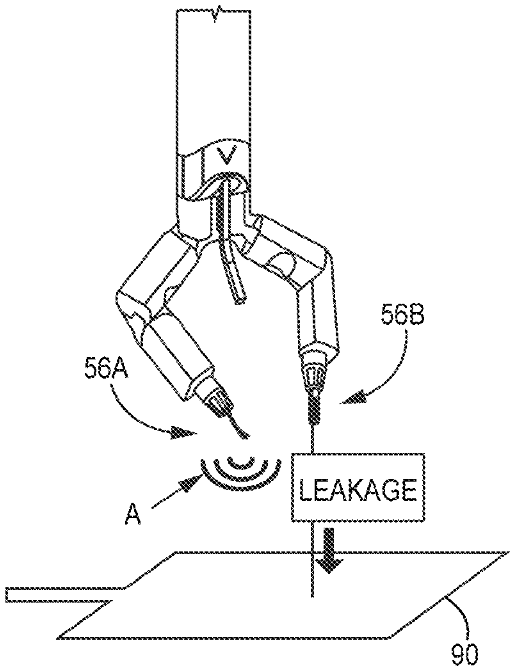
FIG. 4A is a perspective view of a robotic device showing inadvertent electrical current leakage into the left end effector, according to one embodiment.

More specifically, as shown in FIG. 4A (with reference to FIGS. 3A and 3B), the mono-polar cauterization end effector 56A can be actuated (as represented by the lines A) to cauterize a target tissue of the patient, which means that the requisite electrical energy is intended to be transmitted to the end effector 56A along the monopolar elongate conductor 84 (as shown in FIGS. 3A and 3B above). This energy from the monopolar elongate conductor 84 can then inadvertently transfer to the bi-polar elongate conductors 82A, 82B as a result of the coupling Z1 and Z2 discussed above and shown in FIG. 3B. The energy transferred to the bi-polar elongate conductors 82A, 82B can travel along those conductors 82A, 82B to the bi-polar cauterization end effector 56B, thereby resulting in inadvertent actuation of the end effector 56B. That is, some electrical current "leaks" from the bi-polar cauterization end effector 56B as a result of the unintentional transfer of electrical energy from the monopolar conductor 84 to the bi-polar elongate conductors 82A, 82B.

The mono-polar electrical energy transmitted along the monopolar conductor 84 has a very high potential (up to 3,300V), so the coupling of the monopolar conductor 84 to the bipolar conductors 82A, 82B can result in the transfer of significant amounts of current to the bi-polar cauterization end effector (such as end effector 56B) that exceed the limits set by standard. For example, in some embodiments, more than 170 mA is transferred, which exceeds the 50 mA limit set by the standard set forth in the international standard IEC 60601-2-2 by the International Electrotechnical Commission ("IEC"). Alternatively, any known standard may be taken into account with respect to the amount of current transferred.

Figure 4B:
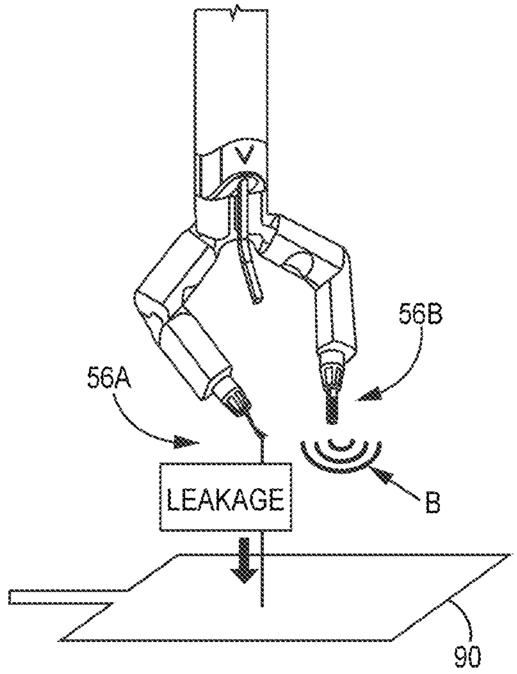
FIG. 4B is a perspective view of a robotic device showing inadvertent electrical current leakage into the right end effector, according to one embodiment.

Similarly, as shown in FIG. 4B, the bi-polar cauterization end effector 56B can be actuated (as represented by lines B) to cauterize a target tissue of the patient, which means that the requisite electrical energy is intended to be transmitted to the end effector 56B along the bi-polar elongate conductors 82A, 82B (as shown in FIGS. 3A and 3B above). This energy from the bi-polar elongate conductors 82A, 82B can then inadvertently transfer to the monopolar elongate conductor 84 as a result of the coupling Z1 and Z2 discussed above and shown in FIG. 3B. The energy transferred to the monopolar elongate conductor 84 can travel along the conductor 84 to the mono-polar cauterization end effector 56A, thereby resulting in inadvertent actuation of the end effector 56A. That is, some electrical current "leaks" from the mono-polar cauterization end effector 56A as a result of the unintentional transfer of electrical energy from the bi-polar elongate conductors 82A, 82B to the monopolar conductor 84.

Figure 5:
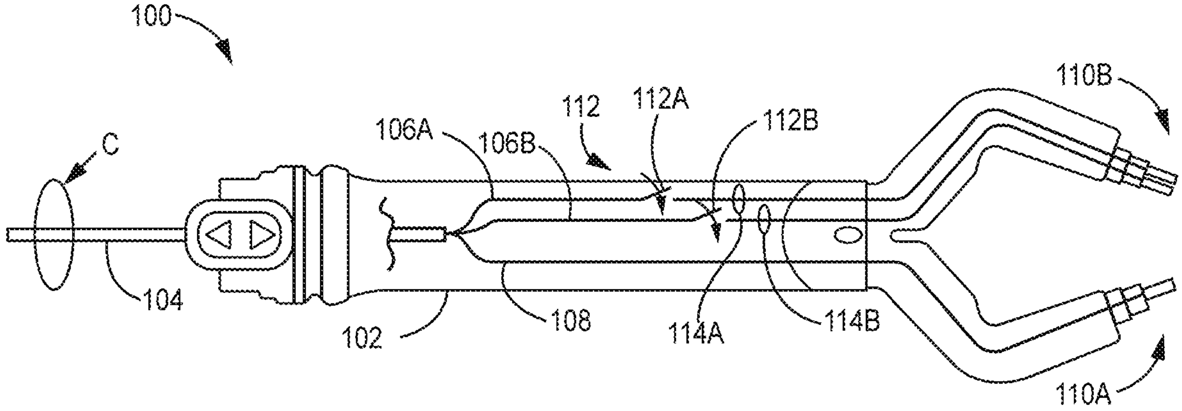
FIG. 5 is a cross-sectional front view of a robotic device with a disconnection system, according to one embodiment.

In one embodiment, a disconnection system 112 is provided to prevent or minimize the type of electrical energy leakage described above. For example, in one specific implementation, the disconnection system 112 is incorporated into a robotic device 100 as depicted in FIG. 5. The disconnection system 112 is positioned along the length of the bi-polar conductors 106A, 106B within the device 100, thereby providing for controllable disconnection of those conductors 106A, 106B from the bi-polar cauterization end effector 110B to prevent transmission of any energy transfer to the end effector 110B. That is, the disconnection system 112 does not prevent the energy transfer described above, because the transfer (represented by the symbol C in FIG. 5) can still occur anywhere along the length of the device cable 104 between the interface pod and electrosurgical unit (similar to the pod and unit 26 discussed above) and the device 100. Instead, the controllable disconnection provided by the system 112 prevents any such energy that has transferred to the bi-polar conductors 106A, 106B from reaching the end effector 110B.

According to one embodiment as shown, the disconnection system 112 is disposed within the body 102 of the device 100. Alternatively, the system 112 can be disposed anywhere within the device.

In this specific implementation as shown schematically in FIG. 5, the disconnection system 112 in this implementation is a set of two disconnection mechanisms 112A, 112B: a first relay 112A coupled to the first bi-polar conductor 106A and a second relay 112B coupled to the second bi-polar conductor 106B. For purposes of this application, the term “relay” is intended to broadly refer to any disconnection mechanism (including for example, any known relay, transistor, switch, etc.) that can be used to disconnect and reconnect any conductor, thereby controlling the ability of conductor to transmit electrical current therethrough.

In use, when the bi-polar electrocautery end effector 110B is actuated, the relays 112A, 112B can be positioned in the closed position to allow electricity to pass along the conductors 106A, 106B to the bi-polar cauterization end effector 110B. Further, when the monopolar electrocauterization end effector 110A is actuated, the relays 112A, 112B can be positioned in the open position (as shown in FIG. 5) such that electricity cannot pass along the conductors 106A, 106B to the end effector 110B, thereby preventing any “leakage” of energy from the monopolar conductor 108 to either or both of the quiescent bi-polar conductors 106A, 106B and thus to the bi-polar cauterization end effector 110B.

A disconnection system (similar to disconnection system 112 or any other disconnection system disclosed or contemplated herein) can also be incorporated into the mono-polar conductor 108 and used to disconnect the conductor 108 from the monopolar cauterization end effector 110A when the mono-polar conductor 108 is the quiescent conductor susceptible to leakage when the bi-polar cauterization end effector 110B is actuated in a fashion similar to the disconnection system 112 discussed above. While the description and the figures set forth herein are focused on the disconnection system 112 (and any other disconnection mechanism embodiments disclosed or contemplated herein) incorporated into the bi-polar conductors 106A, 106B, the various aspects, features, and functionalities of the system 112 (and any other such mechanism herein) can also apply to an equivalent mechanism coupled to the monopolar conductor 108 or any other quiescent conductor in any other robotic device or system with an electrosurgical end effector. Similarly, any disconnection mechanisms disclosed or contemplated herein can also be incorporated into any other elongate conductors in any robotic or medical devices to mitigate energy transfer in a similar fashion.

Additionally, in this exemplary implementation, the disconnect system 112 has current sensors 114A, 114B coupled to the conductors 106A, 106B, respectively. More specifically, the current sensor 114A is coupled to the conductor 106A such that the sensor 114A can detect the amount of electrical current passing through the conductor 106A, and the current sensor 114B is coupled to the conductor 106B such that the sensor 114B can detect the amount of current passing through the conductor 106B.

In certain embodiments, the sensors 114A, 114B are transformers 114A, 114B that supply a current through the secondary winding that is proportional to the current through the primary winding depending on the turns ratio of the transformer. In these embodiments, there is electrical isolation between the current being measured (e.g., the bipolar conductors 106A, 106B) and the system measuring the current (e.g., the system attached to the sensor—such as sensor 114A or sensor 114B). Alternatively, the current sensors 114A, 114B can be any known electrical current sensors, such as Hall effect current sensors, optocouplers, shunt resistors, or any other mechanism capable of measuring electrical current.

In use, the sensors 114A, 114B are coupled to a system controller (such as the electrosurgical unit 26 and console 16 as discussed above, for example) such that the system 10 can track electrical current passing through the conductors 106A, 106B. Thus, if one or both of the disconnection mechanisms 112A, 112B fail, the sensors 114A, 114B will detect the failure. More specifically, the sensors 114A, 114B can detect a failure in which either relay 112A, 112B remains open (such that no electricity can pass) or a failure in which either relay 112A, 112B remains closed (such that electricity continues to pass).

In the event that either or both disconnect circuits 112A, 112B fails in a “closed” position (e.g., either circuit 112A, 112B is unable to disconnect either bipolar conductor 106A, 106B from the bipolar instrument 110B when needed/desired), the current sensors 114A, 114B will detect a leakage current through either of these quiescent conductors 106A, 106B while the monopolar conductor 108 is actuated (such that electrical current is passing through the conductor 108). In some embodiments, this failure is transmitted to the system controller (such as the electrosurgical unit 26 and console 16) such that the controller can be used to take appropriate action. For example, in certain implementations, the controller will immediately disable the electrosurgical generator unit 26, thereby preventing further current from flowing through either of the quiescent conductors 106A, 106B and thus preventing any harm to the patient. In some embodiments, this condition can also trigger an error message to be displayed to the user at the console 16. In some embodiments, upon receiving the failure information, the controller prevents the user from further using the system.

In the event that either or both disconnect circuits 112A, 112B fails in an “open” position (e.g., either circuit 112A, 112B is unable to reconnect the respective bipolar conductor 106A, 106B to the bipolar end effector 110B when necessary/desired), the current sensors 114A, 114B will detect no current flowing, even when the bipolar generator is supplying energy. This failure renders the bipolar instrument 110B inoperable as a result of the inability to pass current through the conductors 106A, 106B to the end effector 110B. This failure, in accordance with certain implementations, is transmitted to the system controller (such as the electrosurgical unit 26 and console 16) such that the controller can be used to take appropriate action. For example, in certain implementations, the controller will transmit an error message to be displayed to the user at the console (such as console 16). Further, in some embodiments, upon receiving the failure information, the controller prevents the user from further using the system.

In certain embodiments, the current sensors 114A, 114B can also be used to enhance the operation of the system 10. More specifically, the system controller (such as the electrosurgical unit 26 and console 16) can use the sensors 114A, 114B as a feedback mechanism to modulate the output power transmitted to the end effector 110B. Thus, the controller can use the sensors 114A, 114B to enhance the consistency of the output power, to counteract any power loss in the either or both of the conductors 106A, 106B, or to provide power adjustments for any other reason based on the feedback from the sensors 114A, 114B.

Figure 6:
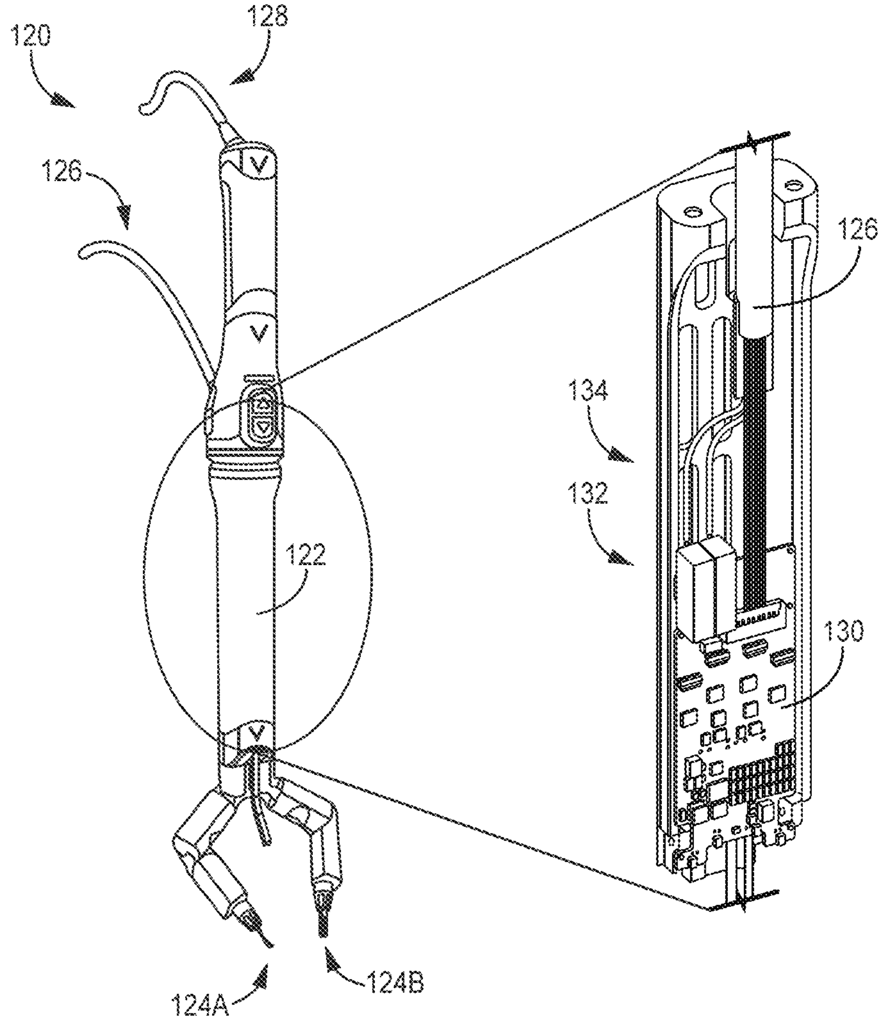
FIG. 6 is a perspective view of a robotic device with an exploded image of a disconnection mechanism that is disposed therein, according to one embodiment.
Figure 7A:
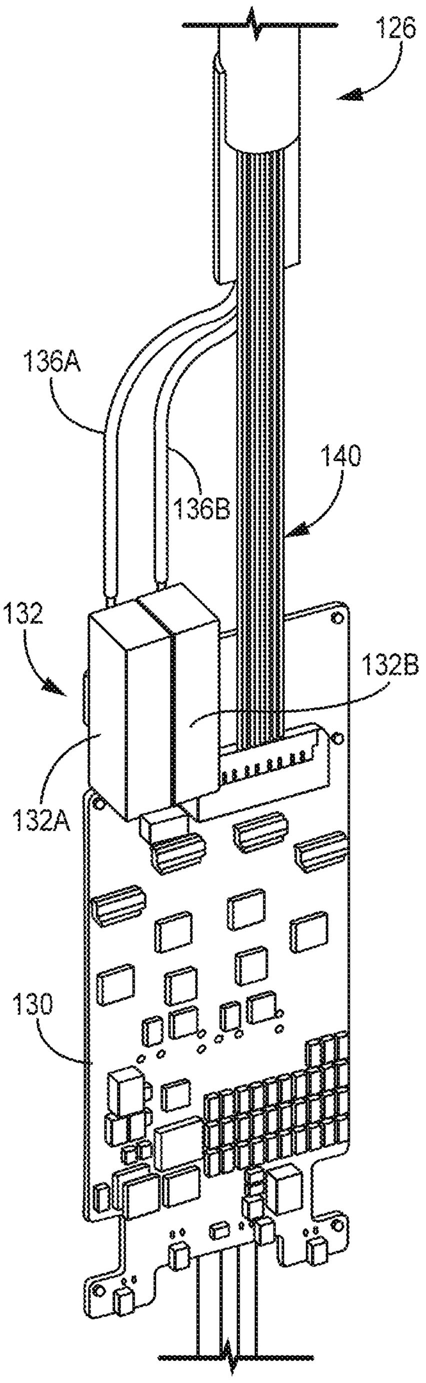
FIG. 7A is a front perspective view of the disconnection mechanism of FIG. 6, according to one embodiment.
Figure 7B:
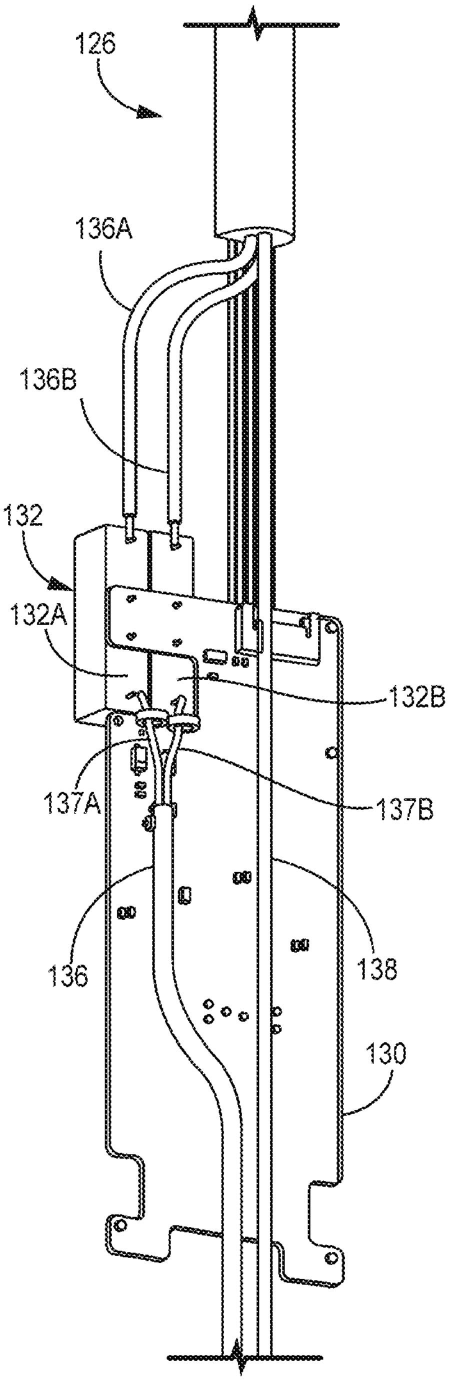
FIG. 7B is a rear perspective view of the disconnection mechanism of FIG. 6, according to one embodiment.
Figure 7C:
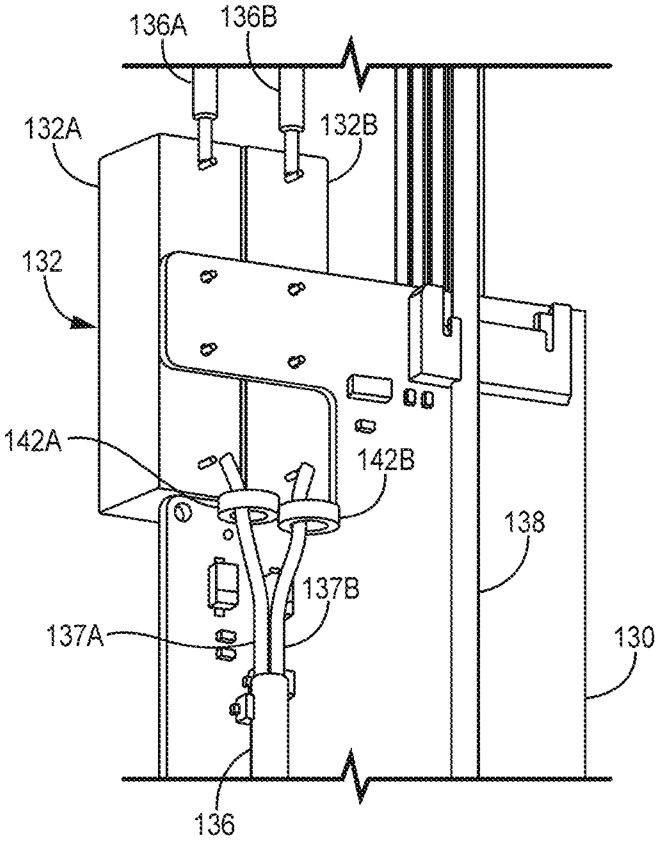
FIG. 7C is an expanded view of the rear of the disconnection mechanism of FIG. 7B, according to one embodiment.
Figure 8:
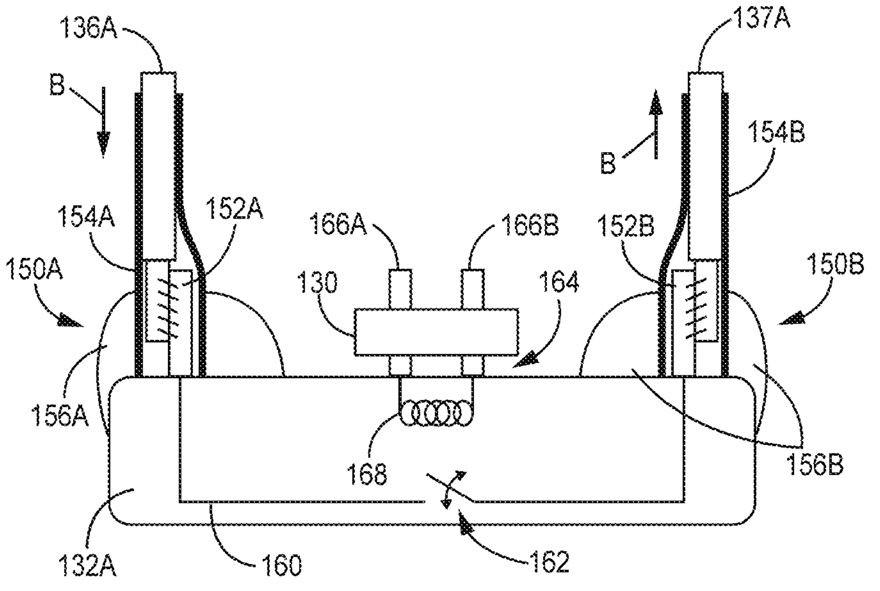
FIG. 8 is a schematic depiction of an exemplary relay housing, according to one embodiment.

In accordance with another implementation as best shown in FIGS. 6-8, a disconnection mechanism 132 can be coupled to, incorporated into, or otherwise associated with a local controller (also referred to herein as a "control board") 130 (such as a printed circuit board 130) of a robotic device 120. In this exemplary embodiment as shown, the control board 130 is disposed within the elongate body 122 of the device as best shown in FIG. 6. More specifically, the board 130 is disposed on a structural support (or "sled") 134 disposed within the body 122. Alternatively, the control board 130 can be disposed within the body 122 in any known fashion and/or coupled to any known structure associated therewith. In various embodiments, this control board 130 can be one of several printed control boards disposed within or otherwise associated with the device 120.

In this specific implementation, the control board 130 can perform many functions for controlling the actuation of the various motors of the device 120 (and thus movement of the arms and other components therein) and for managing the information regarding the device's functionalities and operation. As such, in this specific embodiment, the PCB 130 is coupled to and receives electrical power and signals via the device cable 126. More specifically, as best shown in FIGS. 7A and 7B (which depict the front and back sides of the control board 130, respectively), the device cable 126 ends within the device body 122 such that the various separate conductors therein extend out of the cable 126 inside the body 122. The low voltage signal and power conductors 140 connect directly to the PCB 130, while the mono-polar conductor 138 pass directly though the body 122 and extend into and through the right arm to the right (monopolar cauterization) end effector 124A. As such, in this embodiment, there is no disconnection mechanism coupled to the mono-polar cable 138. However, as mentioned above, in certain alternative implementations, a disconnection mechanism (not shown) could also be coupled to the mono-polar cable 138.

Continuing with FIGS. 7A and 7B, along with exploded view of the back of the control board 130 in FIG. 7C, the disconnection mechanism 132 is comprised of two relay housings (or bodies) 132A, 132B disposed on the control board 130. The conductor 136A is coupled to the relay housing 132A and the conductor 136B is coupled to the relay housing 132B as depicted. More specifically, the two bi-polar conductors 136A, 136B extend through the cable 126 and are coupled at their distal ends to the relay housings 132A, 132B (respectively) of the disconnection mechanism 132. Distally of the relay housings 132A, 132B, the two bi-polar conductors are identified as conductors 137A, 137B and extend from the housings 132A, 132B distally to the end effector as discussed in detail below.

As shown in FIG. 7C, according to one embodiment, the disconnection mechanism 132 can also have a safety mechanism in the form of electrical current sensors 142A, 142B associated with the distal lengths of the bi-polar conductors 137A, 137B. These sensors 142A, 142B can be similar to and operate in a fashion similar to the sensors 114A, 114B discussed above. More specifically, in this exemplary implementation, the sensors 142A, 142B are electrical current sensors 142A, 142B that are disposed around the conductors 137A, 137B on the end effector side of the mechanisms 132. As such, the sensors 142A, 142B can be used to sense whether any current is passing through the disconnection mechanism 132 via the conductors 137A, 137B to the bi-polar cauterization end effector 124B. Any current in the conductors 137A, 137B extending from the mechanism 132 creates a signal that is detected by the sensors 142A, 142B, which are operably coupled to the PCB 130 such that the information about such signals is processed by the device system. Thus, if the disconnection mechanism 132 has been actuated to disconnect the conductors 137A, 137B from the conductors 136A, 136B such that no electricity should be transmitted to the end effector 124B, and yet electrical current is detected by the sensors 142A, 142B, the information is transmitted to the appropriate processor in the system and the transmission of energy along the conductor 138 is stopped. As such, the sensors 142A, 142B are part of a safety mechanism to shut down the actuation of the monopolar cauterization end effector 124A if the disconnection mechanism 132 fails.

Alternatively, any known electrical current sensors can be used in the safety mechanism. In a further alternative, the safety mechanism can be any known safety mechanism for use in such electrical medical devices.

According to one embodiment, one exemplary relay housing 132A (of the two housings 132A, 132B discussed above) is depicted schematically in further detail in FIG. 8. In this specific implementation, the relay housing 132A has isolation barriers (more specifically, a combination of insulation sheaths 154A, 154B and insulation beads 156A, 156B, as discussed in further detail below) that electrically isolate the exemplary housing 132A from the control board 130. It is understood that while the relay housing 132A will be discussed in detail herein with respect to FIG. 8, the second relay housing 132B can have substantially similar components and features (such as the isolation barriers) and operate in substantially the same fashion. The incoming bi-polar conductor 136A is coupled to the housing 132A at a first insulated coupling 150A, and the outgoing bi-polar conductor 137A is coupled to the housing 132A at a second insulated coupling 150B. Both insulated couplings 150A, 150B have a coupling pin 152A, 152B to which the conductors 136A, 137A are physically and electrically coupled. Further, as mentioned above, both insulated couplings 150A, 150B have isolation barriers that consist of an insulation sheath 154A, 154B coupled to and extending along the coupling of the pin 152A, 152B and a length of the end of the conductors 136A, 137A and an insulation bead (or "fillet" or "bonding structure") 156A, 156B. These sheaths 154A, 154B and beads 156A, 156B create the isolation barriers between the base of the pins 152A, 152B and the control board 130. In certain embodiments, the conductors 136A, 137A are soldered to the pins 152A, 152B. Alternatively, the conductors 136A, 137A can be coupled to the pins 152A, 152B using any known coupling mechanism or process.

Each of the insulation sheaths 154A, 154B, in accordance with certain embodiments, has a length sufficient to help create an insulative barrier that prevents current from creeping or otherwise jumping from the pins 152A, 152B along the insulation of either of the conductors 154A, 154B to any other conductive part of the device or system (such as, for example, the control board 130 or the control pins 166A, 166B, which are discussed in further detail below). In one specific example, the sheaths 154A, 154 extend along at least 13.5 mm of the bi-polar conductors 136A, 137A to provide a 4.5 kV isolation barrier per the IEC60601 specification for creepage and clearance distances. Alternatively, the length can be any length that decreases the risk of current creepage, satisfies the desired regulatory standards for the design's isolation voltage rating, or both. According to some implementations, the insulation sheaths 154A, 154B are heat shrink insulation sheaths that can be made of polyolefin, fluoropolymer (such as, for example, FEP, PTFE, or Kynar), PVC, neoprene, silicone elastomer, or Viton. Alternatively, the insulation sheaths 154A, 154B can be made of any known insulation material.

In accordance with various implementations, the bonding structures 156A, 156B are made of an electrically insulating and bonding epoxy, glue, or coating that is applied at an appropriate, known thickness to achieve the desired and/or required dialectric strength and resulting in an insulation barrier between each pin 152A, 152B and other conductive elements of the device or system. In certain embodiments, the insulation barrier is a standards-compliant barrier. For example, according to one exemplary, non-limiting embodiment, each of the structures 156A, 156B are made of Loctite 4090 epoxy, which has a dielectric strength of approximately 500 V/mil. Alternatively, any known epoxy, glue, or coating having an appropriate dialectric strength can be used. In certain embodiments, each structure 156A, 156B has a thickness of at least 9 mil, resulting in a minimum dialectric strength of 4,500V. Alternatively, the structures 156A, 156B each have any thickness that results in sufficient dialectric strength as desired for the design or for standards compliance.

Alternatively, any known insulated couplings having any known configuration can be used.

Continuing with FIG. 8, the exemplary relay housing 132A (also referred to as a "relay") contains an elongate electrical conductor 160 that extends from the first coupling pin 152A to the second coupling pin 152B and includes a actuable switch 162 disposed along the length of the elongate conductor 160. In use, the switch 162 can be positioned in the closed position to allow electricity to pass along the conductor 160 from the incoming bi-polar conductor 136A coupled to the pin 152A to the outgoing bi-polar conductor 137A coupled to the pin 152B. Further, the switch 162 can be positioned in the open position (as shown in FIG. 8) such that electricity cannot pass to the outgoing conductor 137A and thus cannot be transmitted to the end effector 124B, thereby preventing any "leakage" of energy from the end effector 124B.

In one specific implementation, the relay 132A is a Standex-Meder SHV05-1A85-78D4K relay having a contact-to-contact dielectric rating of 4 kV, which is commercially available from Standex Electronics, Inc. in Fairfield, OH. It should be noted that the second relay 132B can also be the same device. Alternatively, the relays 132A, 132B can be any known relays or other types of electrical disconnection mechanisms with an appropriate dialectric rating.

In one embodiment, the housing 132A also has a switch controller 164 that is configured to actuate/urge the switch 162 to move between its open and closed positions as described above. The controller 164 has first and second control pins 166A, 166B that are coupled to the magnetic coil 168 of the relay 132A such that an electrical current can be passed through the pins 166A, 166B and thus through the coil 168 to magnetically urge the switch 162 open or closed. As such, the control board 130 can be used to control the actuable switch 162 by actuating the magnetic coil 168 to urge the switch 162 into either the open or closed position as necessary. According to one implementation, the relay 132A has a contact-to-coil dielectric rating that provides sufficient electrical isolation between the control board 130 and the high voltage bipolar current passing through the relay 132A.

According to certain embodiments, the electrosurgical unit 26 is prevented from operating when the switch 162 is moving between its open and closed position to prevent electrical arcing between the contacts of the switch 162. In various implementations, this failsafe can satisfy the make-or-break voltage rating of the relay, which may be less than the monopolar cautery voltage. Thus, according to some exemplary embodiments, the timing of the closing of the switch 162 is set such that the switch 162 will always be closed when electrical energy is applied across the bi-polar conductor 136A, 137A to actuate the bi-polar end effector.

According to certain implementations, the control board 130 is configured to control the switch 162 to move into the open position and thereby electrically disconnect the proximal bi-polar conductor 136A from the distal bi-polar conductor 137A (and thus the end effector 124B) when the mono-polar end effector 124A is being actuated. More specifically, this disconnection can be automatic—it can be automatically actuated when the mono-polar end effector 124A is actuated. It is understood that the second housing 132B with the second bi-polar conductor 136B, 137B can have a similar configuration. As such, the disconnection housings 132A, 132B provide for disconnection of the proximal lengths of the bi-polar conductors 136A, 136B from the distal lengths of the conductors 137A, 137B in a similar fashion. Alternatively, any known disconnection mechanism (such as mechanical disconnection mechanisms, for example) can be incorporated into each housing 132A, 132B and the actuator can be any known actuator for urging such mechanisms to connect and disconnect the proximal lengths of the conductors 136A, 136B from the distal lengths of the conductors 137A, 137B.

Figure 9A:
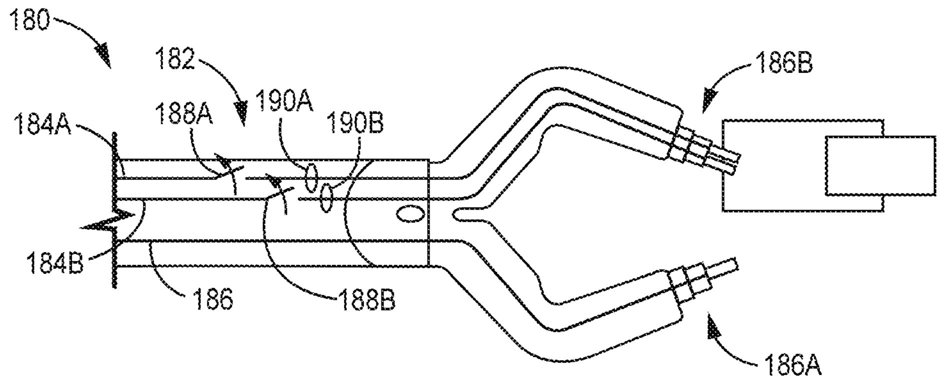
FIG. 9A is a cross-sectional front view of a robotic device with a disconnection mechanism in which the relay switches are open, according to one embodiment.
Figure 9B:
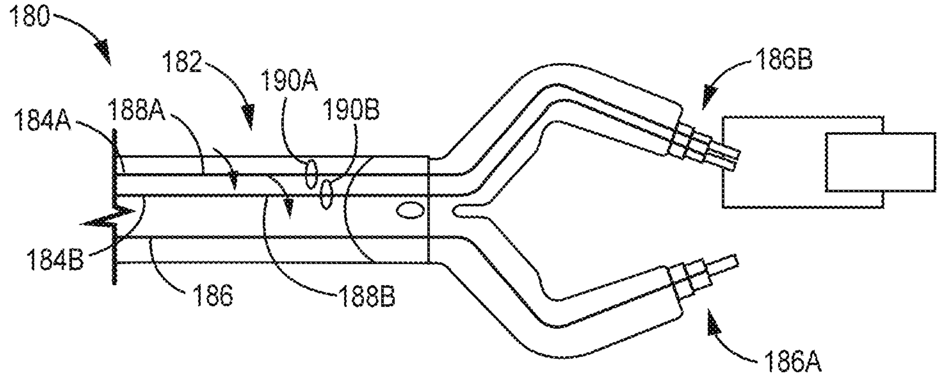
FIG. 9B is a cross-sectional front view of the robotic device with the disconnection mechanism of FIG. 9A in which the relay switches are closed, according to one embodiment.

In use, regardless of the specific configuration, a disconnection mechanism (such as the mechanism 182 in a device 180 as depicted schematically in FIGS. 9A and 9B) is a safety feature that eliminates the problem of the energy from the mono-polar conductor 186 coupling with the bi-polar conductors 184A, 184B such that electrical energy is unintentionally delivered to the surgical target via the bi-polar cauterization end effector 186B. As discussed above, this disconnection mechanism does not stop the energy coupling from occurring along the device cable (such as cable 24A, 104 or 126 as discussed above), but instead prevents any such coupled electrical energy from being transmitted along the bi-polar conductors 184A, 184B to the bi-polar cauterization end effector 186B by eliminating the electrical path to that end effector 186B. Thus, according to certain embodiments, when it is desired to use the bi-polar cauterization end effector 186B, the disconnection mechanism 182 is actuated to close the switches 188A, 188B as shown in FIG. 9B, thereby allowing electrical energy to be transmitted to the end effector 186B. On the other hand, when it is desired to use the monopolar cauterization end effector 186A, the disconnection mechanism can be manually or automatically actuated to open the switches 188A, 188B as shown in FIG. 9A, thereby preventing any electrical energy that may have been transferred to the bi-polar conductors 184A, 184B from the monopolar conductor 186 as a result of energy coupling from actually being transmitted along the bi-polar conductors 184A, 184B to the bi-polar cauterization end effector 186B. Alternatively, as discussed above, the actual mechanisms within the disconnection mechanism 182 can be any known mechanisms for connecting and disconnecting conductive components.

Alternatively, the mitigation devices, features, and methods disclosed or contemplated herein need not be limited to use in a specific robotic surgical device as described herein. Instead, such devices, features, and methods can also be used to mitigate or prevent energy transfer via any type of coupling of any conductors used in any known electrical devices.

While the various systems described above are separate implementations, any of the individual components, mechanisms, or devices, and related features and functionality, within the various system embodiments described in detail above can be incorporated into any of the other system embodiments herein.

The terms "about" and "substantially," as used herein, refers to variation that can occur (including in numerical quantity or structure), for example, through typical measuring techniques and equipment, with respect to any quantifiable variable, including, but not limited to, mass, volume, time, distance, wave length, frequency, voltage, current, and electromagnetic field. Further, there is certain inadvertent error and variation in the real world that is likely through differences in the manufacture, source, or precision of the components used to make the various components or carry out the methods and the like. The terms "about" and "substantially" also encompass these variations. The term "about" and "substantially" can include any variation of 5% or 10%, or any amount—including any integer—between 0% and 10%. Further, whether or not modified by the term "about" or "substantially," the claims include equivalents to the quantities or amounts.

Numeric ranges recited within the specification are inclusive of the numbers defining the range and include each integer within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range. Although the various embodiments have been described with reference to preferred implementations, persons skilled in the art will recognize that changes may be made in form and detail without departing from the spirit and scope thereof.

Although the various embodiments have been described with reference to preferred implementations, persons skilled in the art will recognize that changes may be made in form and detail without departing from the spirit and scope thereof.

What is claimed is:

1. A surgical system, comprising:
a) at least one end effector;
b) at least one conductor coupled to the end effector;
c) a disconnection mechanism associated with the at least one conductor, wherein the mechanism is configured to electrically disconnect the at least one end effector from an energy source when not in use so as to reduce energy leakage, wherein the mechanism comprises a switch, and wherein the mechanism is configured to electrically disconnect the energy source from the at least one end effector when the switch is in an open position; and
d) a controller configured to automatically actuate the switch between the open position and a closed position based on which end effector is being actuated.

2. The surgical system of claim 1, wherein the controller is configured to adjust output power transmitted to the at least one end effector to counteract power loss in the at least one conductor.

3. The surgical system of claim 1, wherein the disconnection mechanism is an electrical relay.

4. The surgical system of claim 1, wherein the end effector is a bi-polar end effector.

5. The surgical system of claim 1, wherein the end effector is a monopolar end effector.

6. The surgical system of claim 1, wherein the at least one end effector comprises two end effectors.

7. The surgical system of claim 1, wherein the end effector is an electrosurgical end effector.

8. The surgical system of claim 1, further comprising an electrical current sensor coupled to the at least one conductor, wherein the electrical current sensor is disposed between the disconnection mechanism and the end effector.

9. The surgical system of claim 8, wherein the electrical current sensor comprises a transformer current sensor, a Hall Effect current sensor, or a shunt resistor.

10. The surgical system of claim 8, wherein the controller of the surgical system is operably coupled to the electrical current sensor, wherein the controller is configured to receive information from the electrical current sensor and modulate energy delivery from the energy source to the end effector based on the information from the electrical current sensor.

11. The surgical system of claim 10, wherein the controller is configured to shut down the energy source when a disconnection mechanism failure is detected at the electrical current sensor.

12. The surgical system of claim 1, wherein the controller is configured to prevent the energy source from operating while the switch is moving from the open position to the closed position, such that electrical energy is applied to the at least one conductor after the switch reaches the closed position.

13. A robotic surgical device comprising:
a) an elongate device body;
b) a first robotic arm operably coupled to the elongate device body, the first robotic arm comprising a first end effector operably coupled to the first robotic arm;
c) a first conductor coupled to the first end effector, the first conductor comprising:

i) a proximal length disposed within the elongate device body and extending out of a proximal portion of the device body to an external energy source; and ii) a distal length disposed within the elongate device body and extending out of a distal portion of the device body and through the first robotic arm to the first end effector;

d) a disconnection mechanism disposed within the elongate device body and coupled with the proximal length and the distal length of the first conductor, wherein the disconnection mechanism comprises a switch comprising an open position and a closed position, and wherein the disconnection mechanism is configured to electrically disconnect the external energy source from the first end effector when the switch is in the open position; and e) a controller configured to automatically actuate the switch between the open position and the closed position based on which end effector is being actuated.

14. The robotic surgical device of claim 13, wherein, when the switch is in the open position, the distal length is electrically disconnected from the proximal length of the first conductor.

15. The robotic surgical device of claim 13, wherein the disconnection mechanism is an electrical relay.

16. The robotic surgical device of claim 13, wherein the first end effector is a bi-polar end effector or a monopolar end effector.

17. The robotic surgical device of claim 13, further comprising an electrical current sensor coupled to the distal length of the first conductor.

18. The robotic surgical device of claim 17, wherein the controller of the surgical system is operably coupled to the electrical current sensor, wherein the controller is configured to receive information from the electrical current sensor and modulate energy delivery from the external energy source to the first end effector based on the information from the electrical current sensor.

19. The robotic surgical device of claim 18, wherein the controller is configured to shut down the external energy source when a disconnection mechanism failure is detected at the electrical current sensor.

20. The robotic surgical device of claim 13, further comprising a second robotic arm operably coupled to the elongate device body, the second robotic arm comprising a second end effector operably coupled to the second robotic arm.

* * * * *